US006447265B1

(12) United States Patent
Antaki et al.

(10) Patent No.: US 6,447,265 B1
(45) Date of Patent: Sep. 10, 2002

(54) MAGNETICALLY SUSPENDED MINIATURE FLUID PUMP AND METHOD OF DESIGNING THE SAME

(75) Inventors: James F. Antaki, Allison Park, PA (US); Bradley Paden, Santa Barbara, CA (US); Gregory Burgreen, Pittsburgh, PA (US); Nelson Groom, White Marsh, VA (US)

(73) Assignees: The University of Pittsburgh, Pittsburg, PA (US); The United States of America as represented by the United States National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/398,878

(22) Filed: Sep. 20, 1999

Related U.S. Application Data

(62) Division of application No. 08/673,627, filed on Jun. 26, 1996, now Pat. No. 6,015,272.

(51) Int. Cl.[7] .......................... F04B 17/00; F03B 13/00
(52) U.S. Cl. .................... 417/354; 417/356; 417/423.1; 417/423.12; 415/900
(58) Field of Search ................. 417/356, 352, 417/353, 354, 423.7, 423.12, 410.1; 415/900, 10, 91, 200, 218.1, 219, 221; 416/3, 241 R

(56) References Cited

U.S. PATENT DOCUMENTS

| | | | |
|---|---|---|---|
| 2,500,400 A | * | 3/1950 | Cogswell .................. 415/91 |
| 3,143,972 A | | 8/1964 | Smith et al. .............. 415/91 |
| 3,155,437 A | | 11/1964 | Kinsey et al. |
| 3,433,163 A | * | 3/1969 | Sheets et al. ............. 417/353 |
| 3,647,324 A | | 3/1972 | Rafferty et al. |
| 3,823,990 A | | 7/1974 | Gillinson, Jr. |
| 3,877,761 A | | 4/1975 | Boden et al. |
| 4,088,018 A | | 5/1978 | Anderson et al. |
| 4,156,548 A | | 5/1979 | Anderson et al. |
| 4,382,199 A | | 5/1983 | Isaacson |
| 4,625,712 A | | 12/1986 | Wampler |
| 4,683,391 A | | 7/1987 | Higuchi |
| 4,688,998 A | | 8/1987 | Olson et al. |

(List continued on next page.)

FOREIGN PATENT DOCUMENTS

DE 33 43 186 A1 5/1985

OTHER PUBLICATIONS

Antaki, J.F., "The steamliner," *Pitt. Medicine*, 1995, 12–15.
Hamilton, J., "Can we end heart disease," *Business Week*, 1997, 106–108 and 110–111.
Paula, G., "The mechanics of anatomy," *Medical Engineering*, 1998, 81–83.

(List continued on next page.)

*Primary Examiner*—Cheryl J. Tyler
(74) *Attorney, Agent, or Firm*—Woodcock Washburn Kurtz Mackiewicz & Norris LLP

(57) ABSTRACT

A rotary pump for pumping fluids through a patient having a housing with an internal region, a stator member and an impeller positioned within the housing and having impeller blades, wherein the impeller is magnetically suspended and rotated, and wherein the geometric configuration of the rotary pump is sized and proportioned to minimize stagnant and traumatic fluid flow within the rotary pump. The plurality of magnetic impeller blades are preferably rare earth, high-energy-density magnets selected from the group consisting of samarium cobalt and neodymium-iron-boron alloy.

24 Claims, 22 Drawing Sheets

U.S. PATENT DOCUMENTS

| | | |
|---|---|---|
| 4,704,121 A | 11/1987 | Moise |
| 4,763,032 A | 8/1988 | Bramm et al. |
| 4,779,614 A * | 10/1988 | Moise .................. 417/356 |
| 4,817,586 A | 4/1989 | Wampler |
| 4,846,152 A | 7/1989 | Wampler et al. |
| 4,895,557 A | 1/1990 | Moise et al. |
| 4,908,012 A | 3/1990 | Moise et al. |
| 4,944,722 A | 7/1990 | Carriker et al. |
| 4,944,748 A | 7/1990 | Bramm et al. |
| 4,957,504 A | 9/1990 | Chardack |
| 4,994,017 A | 2/1991 | Yozu |
| 4,994,078 A * | 2/1991 | Jarvik .................. 415/900 |
| 4,995,857 A | 2/1991 | Arnold |
| 5,003,211 A | 3/1991 | Groom |
| 5,003,235 A | 3/1991 | Groom |
| 5,043,643 A * | 8/1991 | Hedlund et al. ......... 318/254 |
| 5,049,134 A | 9/1991 | Golding et al. |
| 5,055,005 A | 10/1991 | Kletschka |
| 5,078,741 A | 1/1992 | Bramm et al. |
| 5,092,879 A | 3/1992 | Jarvik |
| 5,098,256 A | 3/1992 | Smith |
| 5,111,102 A | 5/1992 | Meeks |
| 5,112,200 A | 5/1992 | Isaacson et al. |
| 5,112,202 A | 5/1992 | Oshima et al. |
| 5,112,292 A | 5/1992 | Hwang et al. |
| 5,112,349 A | 5/1992 | Summers et al. |
| 5,118,264 A | 6/1992 | Smith |
| 5,145,333 A | 9/1992 | Smith |
| 5,195,877 A | 3/1993 | Kletschka |
| 5,209,650 A | 5/1993 | Lemieux |
| 5,211,546 A * | 5/1993 | Isaacson et al. ......... 415/900 |
| 5,267,940 A | 12/1993 | Moulder |
| 5,275,580 A | 1/1994 | Yamazaki |
| 5,282,849 A | 2/1994 | Kolff et al. |
| 5,290,227 A | 3/1994 | Pasque |
| 5,300,841 A | 4/1994 | Preston et al. |
| 5,326,344 A | 7/1994 | Bramm et al. |
| 5,344,443 A | 9/1994 | Palma et al. |
| 5,376,114 A | 12/1994 | Jarvik |
| 5,385,581 A | 1/1995 | Bramm et al. |
| 5,441,535 A | 8/1995 | Takahashi et al. |
| 5,443,503 A | 8/1995 | Yamane |
| 5,470,208 A | 11/1995 | Kletschka |
| 5,507,629 A | 4/1996 | Jarvik |
| 5,527,159 A * | 6/1996 | Bozeman, Jr. et al. ...... 415/900 |

OTHER PUBLICATIONS

Backers, F.T., "A Magnetic Journal Bearing," *Phillips Technical Review*, 1960–61, 22(7), 232–238.

Ball Brothers Research Corporation, *Annular Momentum control Device (AMCD)*, Laboratory Model Development, NASA CR–144917, 1976, vol. 1, 4–6–4–9.

Burgreen, G.W. et al., "CFD–Based Design Optimization of a Three Dimensional Rotary Blood Pump," AIAA Paper No. 96–4185, 1996, 1773–1778.

Gurumoorthy, R. et al., "Implementation of Sensorless Control of Radial Magnetic Bearings," *Proceedings of MAG '95*, Alexandria, Aug. 1994, 239–248.

Henrikson, C.H. et al., "Magnetically Suspended Memementum Wheels for Spacecraft Stabilization," presented at the AIA 12th Aerospace Sciences Meetings, Washington, D.C., Jan. 30–Feb. 1, 1974, Paper No. 74–128, pp. 1–8.

Okado, Y. et al., "Sensorless Magnetic Levitation Control by Measuring the PWM Carrier Frequency Content," *Proceedings of the Third International Symposium on Magnetic Bearings* Alexandria, Jul. 1992, 176–183.

Vischer, D. et al., "A New Approach to Sensorless and Voltage Controlled AMBs Based on Network Theory Concept," *2nd International Conference on Magnetic Bearings*, Tokyo, Jul. 1990, 301–306.

Yonnet, J.P. et al., "Stacked Structures of Passive Magnet Bearings," *J. Appl. Physics*, 1991, 70(10), 6633–6635.

Dieter Vischer, Hannes Bleuler; "A New Approach to Sensorless and Voltage Controlled AMBs Based On Network Theory Concepts"; *2nd International Symposium on Magnetic Bearing*; 1990; pp. 301–306.

* cited by examiner

FIG.3
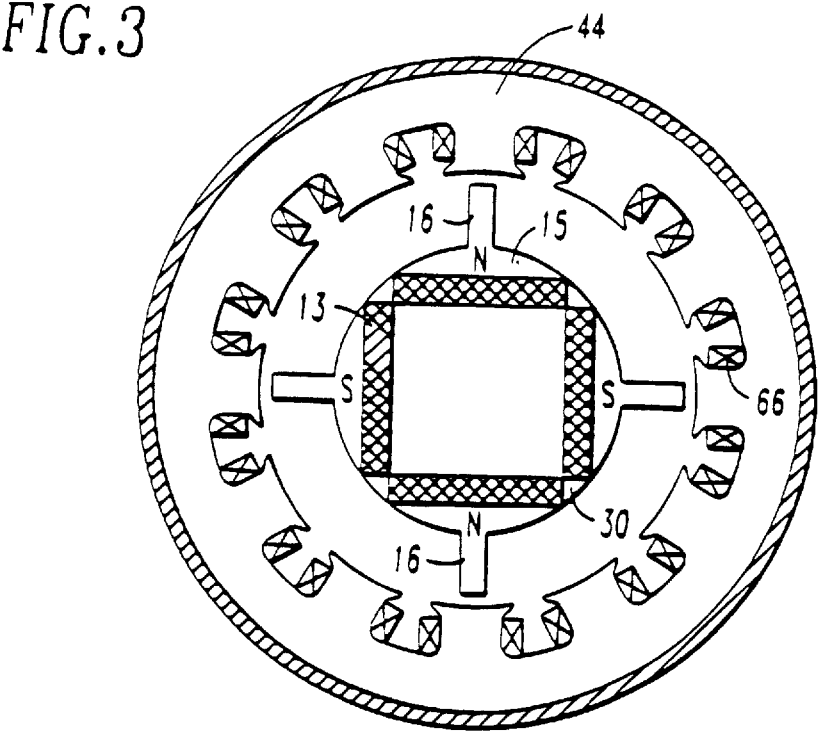
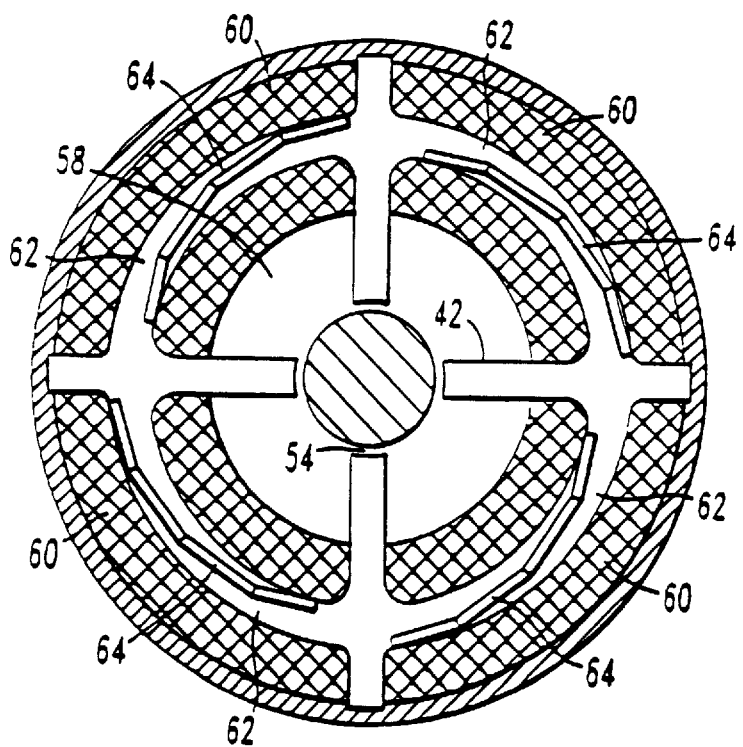
FIG.4

FIG.24
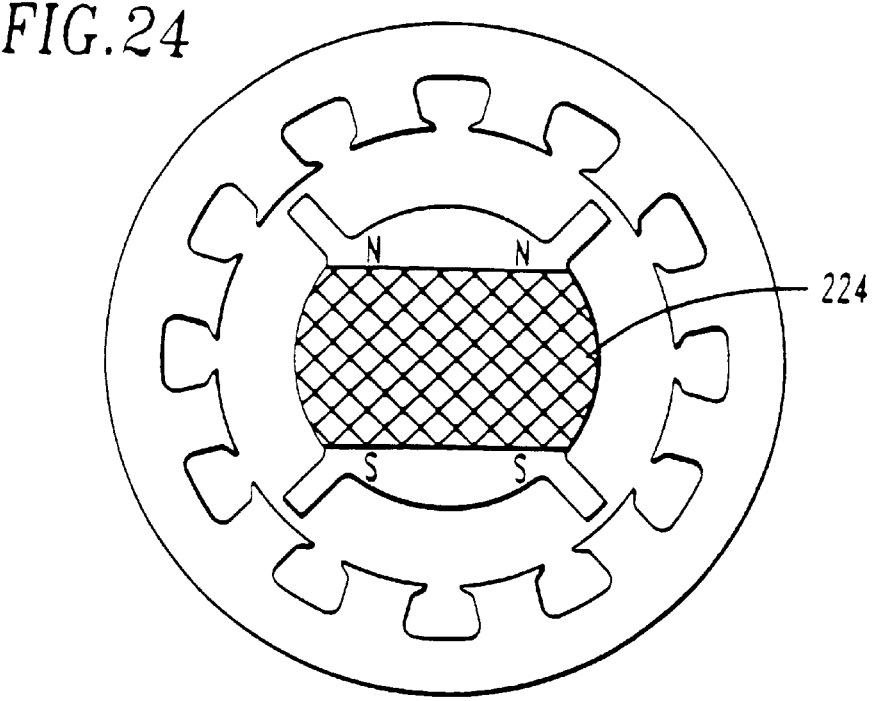
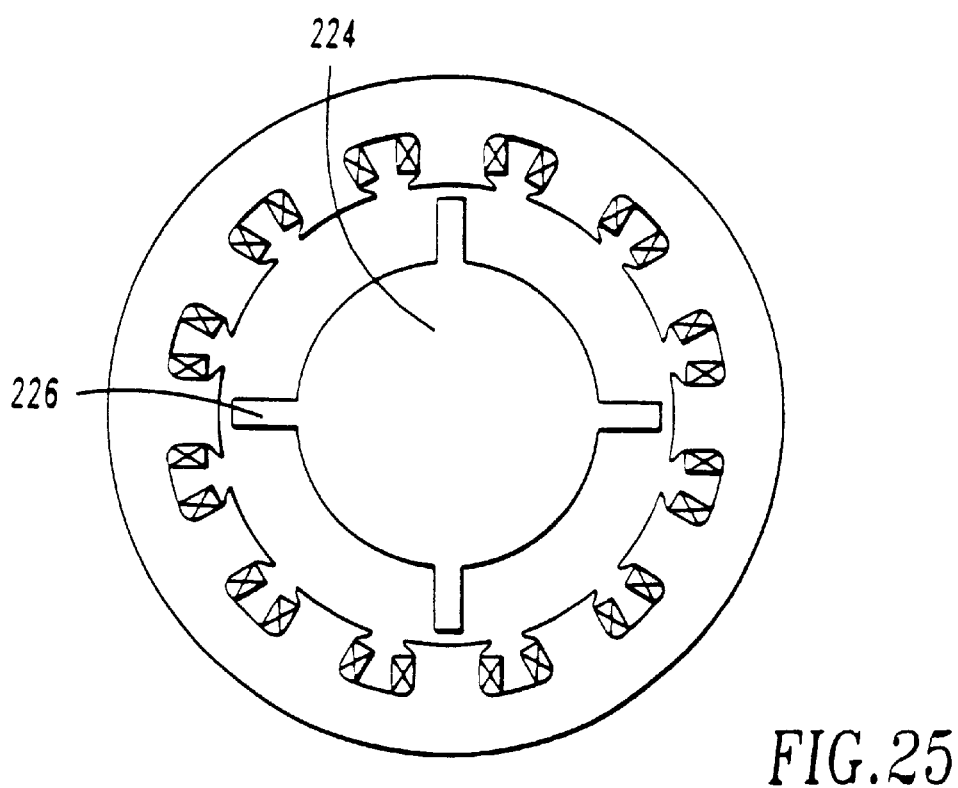
FIG.25

MAGNETICALLY SUSPENDED MINIATURE FLUID PUMP AND METHOD OF DESIGNING THE SAME

This Application is a divisional of application Ser. No. 08/673,627 filed Jun. 26, 1996 entitled "Magnetically Suspended Miniature Fluid Pump and Method Of Making the Same" now U.S. Pat. No. 6,015,272.

This invention described herein was jointly made by employees of the United States Government and by employees of University of Pittsburgh, and it may be manufactured and used by or for the United States Government purposes without payment of royalties thereon or therefor.

BACKGROUND OF THE INVENTION

1. Field of the Invention

This invention relates to a rotary fluid pump having a magnetically suspended and rotated impeller and a method of making the same. More particularly, this invention concerns a rotary fluid pump comprising a housing, an impeller having magnetic impeller blades, a stator member attached to the housing, means for levitating the impeller such that the impeller is substantially centered within the housing, and means for rotating the impeller, and wherein the geometric configuration of the rotary fluid pump is sized and proportioned to minimize stagnant and turbulent fluid flow.

2. Description of the Related Art

The use of a rotary pump ventricular assist device for aiding a patient's heart in pumping blood is well known. The rotary pump ventricular assist device may be connected to the patient's heart in a left-ventricular assist configuration, or a right-ventricular assist configuration, or a bi-ventricular assist configuration. For instance, if the left-ventricular assist configuration is adopted, the rotary pump is connected between the left ventricle of the patient's heart and the aorta. Generally, the rotary pump comprises a housing having an inlet and an outlet, an impeller positioned within the housing and having impeller blades, and a stator member. The blood enters the inlet of the housing and is pumped by the rotating impeller through the housing to the outlet and into the patient's circulatory system.

Artificially pumping blood utilizing a rotary pump may be detrimental to the blood. If the rotary pump is inefficient, the pump will impart excessive entropy to the blood which usually takes the form of heat or fracture. The heat produced from the pump can damage the blood. The blood cells may coagulate or the albumin of the blood may denature if the temperature reaches forty-two degrees centigrade (42° C.).

Moreover, numerous studies have proven that exposing blood to high stresses results in direct or delayed destruction of blood. As a result of the rotation of the impeller, regions of turbulence, jet formation, cavitation and rapid acceleration may be created and cause the blood cells flowing through the pump to break down and rupture. Also, the geometric configuration of a rotary pump may contribute to regions of retarded flow being formed, such as, recirculation and stagnation which cause blood to deposit on the pump structure resulting in thrombosis.

Many attempts have been made to overcome the above-mentioned disadvantages of utilizing a rotary pump as a ventricular assist device. One type of conventional rotary pump utilizes mechanical bearings that necessitate a lubricant flush or purge with an external lubricant reservoir for lubricating the bearing and minimizing heat generation. Examples of this type of rotary pump are illustrated in U.S. Pat. Nos. 4,944,722 and 4,846,152 issued to Carriker et al. and Wampler et al., respectively. There are many disadvantages to this type of rotary pump. The percutaneous supply of the lubricant purge fluid degrades the patient's quality of life and provides a potential for infection. Seals for the external lubricant are notoriously susceptible to wear and to fluid attack which may result in leakage and the patient having a subsequent seizure. Also, an additional pump is needed for delivery of the lubricant to the bearing. Yet another disadvantage of this type of rotary pump is that the bearings will need to be replaced over time because of wear due to the bearings directly contacting other pump structure.

In order to eliminate the need for an external purge of lubricant, a rotary fluid pump having a magnetically suspended impeller was created. By utilizing a magnetically suspended impeller, direct contact between the bearing and other pump structures, as well as external lubricant purges are eliminated. Examples of this type of rotary fluid pump are disclosed in U.S. Pat. Nos. 5,326,344 and 4,688,998 issued to Bramm et al. and Olsen et al., respectively. This type of rotary pump generally comprises an impeller positioned within a housing, wherein the impeller is supported and stabilized within the housing by a combination of permanent magnets positioned in the impeller and the housing and an electromagnet positioned within the housing. The impeller is rotated by a ferromagnetic stator ring mounted within the housing and electromagnetic coils wound around two diametrically opposed projections. The ferromagnetic impeller and the electromagnetic coils are symmetrically positioned with respect to the axis of the rotary pump and thus, impose an axially symmetric force on the fluid passing through a single annular gap formed between the housing and the impeller. The disadvantage of this type of rotary pump is that there is only one annular gap for the blood to pass through and it serves competing purposes with respect to fluid flow and the magnetic suspension and rotation of the impeller. Regarding fluid flow, the cap is desired to be large for efficient pumping whereas, for efficient suspension and rotation of the impeller, the gap is desired to be small. In this type of rotary pump, the fluid gap is relatively small and does not allow for efficient pumping of blood therethrough which may result in the destruction of blood cells.

The pursuit of designing a rotary pump which is sized and proportional to satisfy the competing requirements of providing satisfactory hydrodynamic performance and blood bio-compatibility, as well as efficient magnetic levitation and rotation of the impeller, involves the manipulation of numerous design parameters, arguably more than the human designer can manage at one time. The conventional process for designing a rotary fluid pump limits the focus of the design parameters and relies heavily on first order principles, such as Bernoulli's equation and Euler's equation, empirical analyses and trial-and-error methods. A prototype of a pump design based substantially on intuition is created and subjected to testing. Only when a fluid exhibiting the characteristics of blood is pumped through the prototype pump is it clear whether the design is viable. Because the cost of building a prototype is usually high and typically multiple prototypes are created and tested before a final, viable pump is completed, the process can be quite expensive and time-consuming. Furthermore, the best design of the infinite number of options is not guaranteed using this process.

Nowhere in the cited related art is there disclosed or suggested a rotary pump for pumping blood through a patient having a magnetically suspended and rotated impeller, wherein the geometric configuration of the pump provides for blood flow that is hydrodynamically and biocompatibly satisfactory and a method of making the same. Therefore, there is a definite need for a rotary pump having a magnetically suspended and rotated impeller that pumps fluid without creating regions of stagnant and turbulent fluid flow and a method of making the same.

SUMMARY OF THE INVENTION

Accordingly, the present preferred invention provides a rotary pump for pumping fluid through a patient having a magnetically suspended and rotated impeller and a pump configuration that minimizes blood trauma and stagnant flow while providing efficient magnetic suspension and rotation of the impeller.

The present preferred invention provides a rotary pump for pumping fluids through a patient substantially comprising a housing, an impeller positioned within the housing and having a plurality of magnetic impeller blades, a stator member, means for levitating the impeller within the housing such that the impeller is substantially centered therein, and means for rotating the impeller, and wherein the geometric configuration of the rotary pump is sized and proportioned to minimize trauma to the blood and stagnant fluid flow through the rotary pump. The plurality of magnetic impeller blades serve the dual purpose of imparting mechanical energy to the blood and providing a flux path for the means of rotating the impeller. The plurality of magnetic impeller blades are preferably a rare earth, high-energy-density type magnet selected from the group consisting of samarium cobalt and neodymium-iron-boron alloy which reduces the effects of magnetic leakage. Alternatively, the impeller blades are made from soft magnetic material such as silicon-iron or cobalt-iron. This material can carry flux densities which are higher than the remanence of the best available permanent magnetic material. Thus, thinner blades can be used for improving blood flow and increasing the efficiency of the motor. Magnets are embedded in the body of the impeller and the impeller blades are attached to these magnets by a flux focusing structure made of soft magnetic material.

The present preferred invention provides for a primary fluid flow region that is large enough to provide for hydrodynamically efficient fluid flow without traumatic or turbulent fluid flow and a magnetic gap which also allows for fluid therethrough without traumatic or turbulent flow and which is small enough to provide for efficient magnetic levitation of the central hub which can be either the stator or the impeller. The magnetic gap can be positioned at the housing or adjacent the hub wherein the hub member can be either the impeller or the stator.

The present preferred invention provides that the individual parts of the rotary pump such as, the impeller and the stator member are designed using a computational fluid dynamics-based design method. Specifically, the geometric configuration of each of the parts of the rotary pump are designed taking into consideration the specific flow characteristics of blood while minimizing trauma, platelet activation and turbulence which are measured by high shear stress with respect to residence time, viscous energy dissipation rate, particle acceleration, negative pressure causing outgassing or cavitation, vorticity, reverse flow (i.e., boundary layer shear locally becoming zero), adverse pressure gradient, the standard deviation of consecutive blade-to-blade axial velocity and boundary layer transport.

The present preferred invention provides an embodiment wherein the stator member has an upstream set of stationary blades and a downstream set of stationary blades, wherein each set of stationary blades serve as magnetic bearing poles. Each of the sets of stationary blades converge around the impeller such that each set defines a magnetic bearing gap across which a magnetic force is applied. This embodiment also provides for the impeller to be substantially axially symmetric having a conical-shaped nose and a conical-shaped tail wherein the converging ends of each of the sets of the stationary blades correspond to the shape of the impeller nose and the impeller tail. Preferably, the impeller blades and both sets of the stationary blades are soft magnetic material and are attached to permanent magnets in the body of the impeller.

The present preferred means for rotating the impeller and means for levitating the impeller employ a mix of electromagnets and permanent magnets in order to minimize the heat generated by the rotary pump that may result in the degradation of blood cells. Preferably, the levitating means comprises a plurality of coils wound around a plurality of backiron segments, magnetic targets positioned on the impeller, a downstream set of magnetic stationary blades and an upstream set of magnetic stationary blades. It is preferred that the levitating means further comprises a plurality of permanent magnets positioned within the backiron segments to create a permanent magnetic bias thus, reducing the steady state current in the plurality of coils. The rotating means can take many forms, such as a variable reluctance motor brushles3 DC motor or an induction motor. Preferably the means for rotating is a brushless DC motor.

The present preferred invention of the rotary pump further provides for a magnetic bearing controller which senses axial and radial movement of the impeller within the housing and repositions the impeller to its centered position within the housing. It is preferred that a controller of minimal complexity be used in which the control is decoupled as follows: (1) linearly transforming the sensors signals electronically or by microprocessor software into five (5) signals corresponding to the x and z motion of the impeller nose, the x and z motion of the impeller tail, and the y motion of the impeller; (2) independently compensating each of these five signals (e.g. proportional-integral-derivative control or magnetic bearing zero-power control); (3) transforming the resulting five signals into current patterns which are summed and applied to the bearing coils wherein the current patterns are chosen such that they result in a force being applied on the impeller which substantially centers the impeller within the housing. For example, the response to a positive displacement in the y direction is a coil current pattern which produces a restoring force in the negative y direction. The linear operation which transforms the sensor signals into the five (5) decoupled displacements and the linear operations which transforms a compensator outputs to coil current patterns preferably is represented as matrix multiplications which are referred to as decoupling matrices. The resulting feedback control may be designed to stably position the impeller in the center of the housing. Related methods are being done by MECOS Traxler, Inc.

The present preferred invention further provides another embodiment of the rotary pump having an impeller with an interior wall defining a void, an exterior wall, outboard blades extending from the exterior wall and inboard blades extending from the interior wall, wherein the stator member extends within the impeller and has stationary blades that are attached to the housing.

The present preferred invention further provides for the rotary pump to be connected to the patient's heart using an inflow canula having a trumpet mouth nozzle and a substantially hourglass exterior configuration. A second outflow cannula may be attached to the outlet of the housing of the rotary pump. The inflow cannula is intended to minimize leading edge separation between the heart and the rotary pump which can occur with traditional sharp-edged cannula tips. The concave feature of the hourglass configuration assists in the location of the nozzle within the myocardium by placing the nozzle within the heart and then slightly withdrawing the nozzle until a slight resistance is detected.

Other details, objects and advantages of the present preferred embodiments and the method of making the same will become more apparent with the following description of the present preferred invention.

BRIEF DESCRIPTION OF THE DRAWINGS

The accompanying drawings show the present preferred embodiments of the invention in which:

FIG. 3 is a cross-sectional view of the motor stator and rotor of the rotary fluid pump shown in FIG. 1 taken along line III—III.

FIG. 4 is a cross-sectional view of the stator member and impeller of the rotary fluid pump shown in FIG. 1 taken along line IV—IV.

FIG. 24 is a cross-sectional view of a two-pole motor having four impeller blades which is an alternative motor for the rotary pump shown in FIG. 1.

FIG. 25 is a cross-sectional view of a variable reluctance motor hybridized with impeller blades.

DETAILED DESCRIPTION OF THE PRESENT PREFERRED INVENTION

Figure 1:
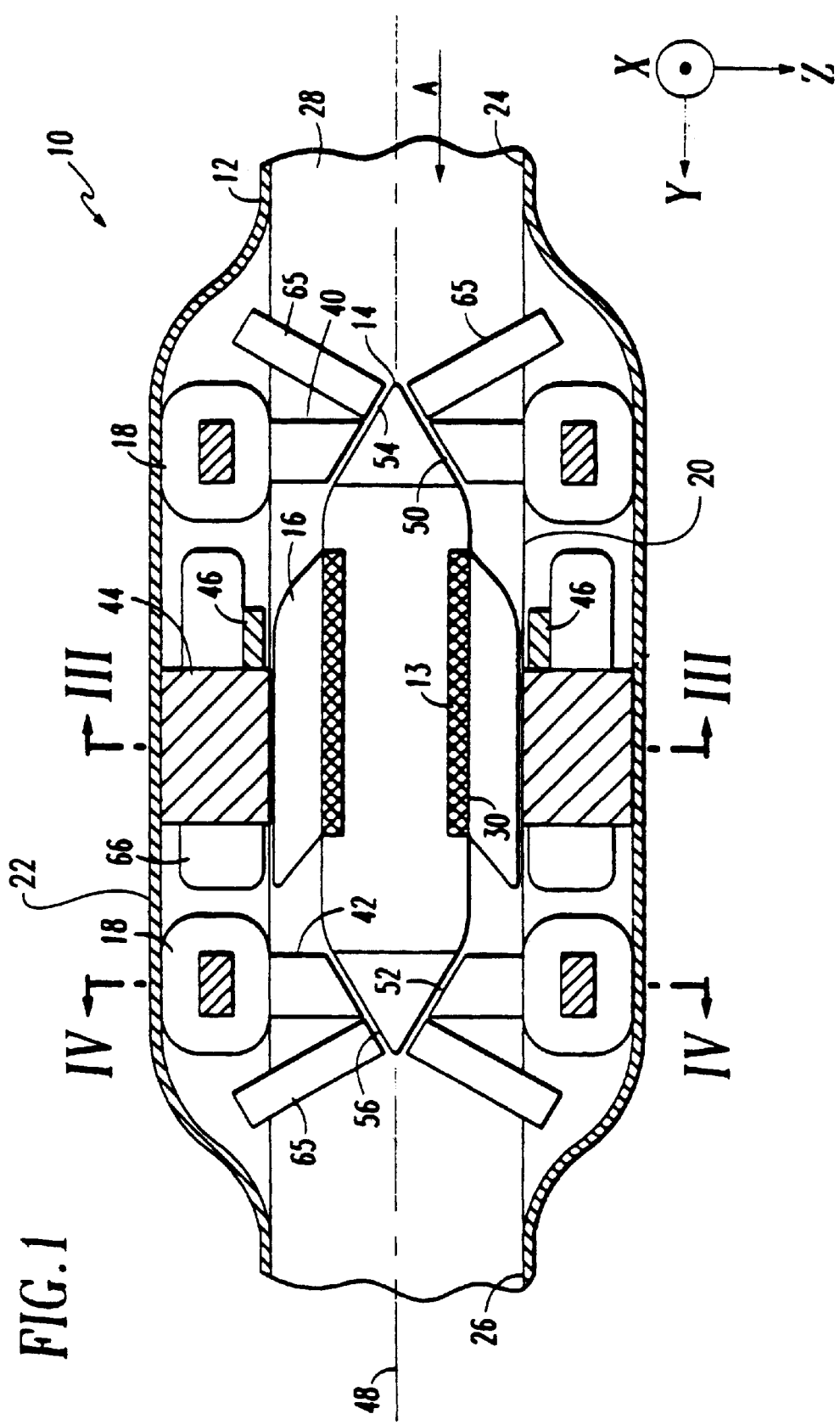
FIG. 1 is a cross-sectional view of a present preferred embodiment of a rotary fluid pump having a magnetically suspended impeller.
Figure 2:
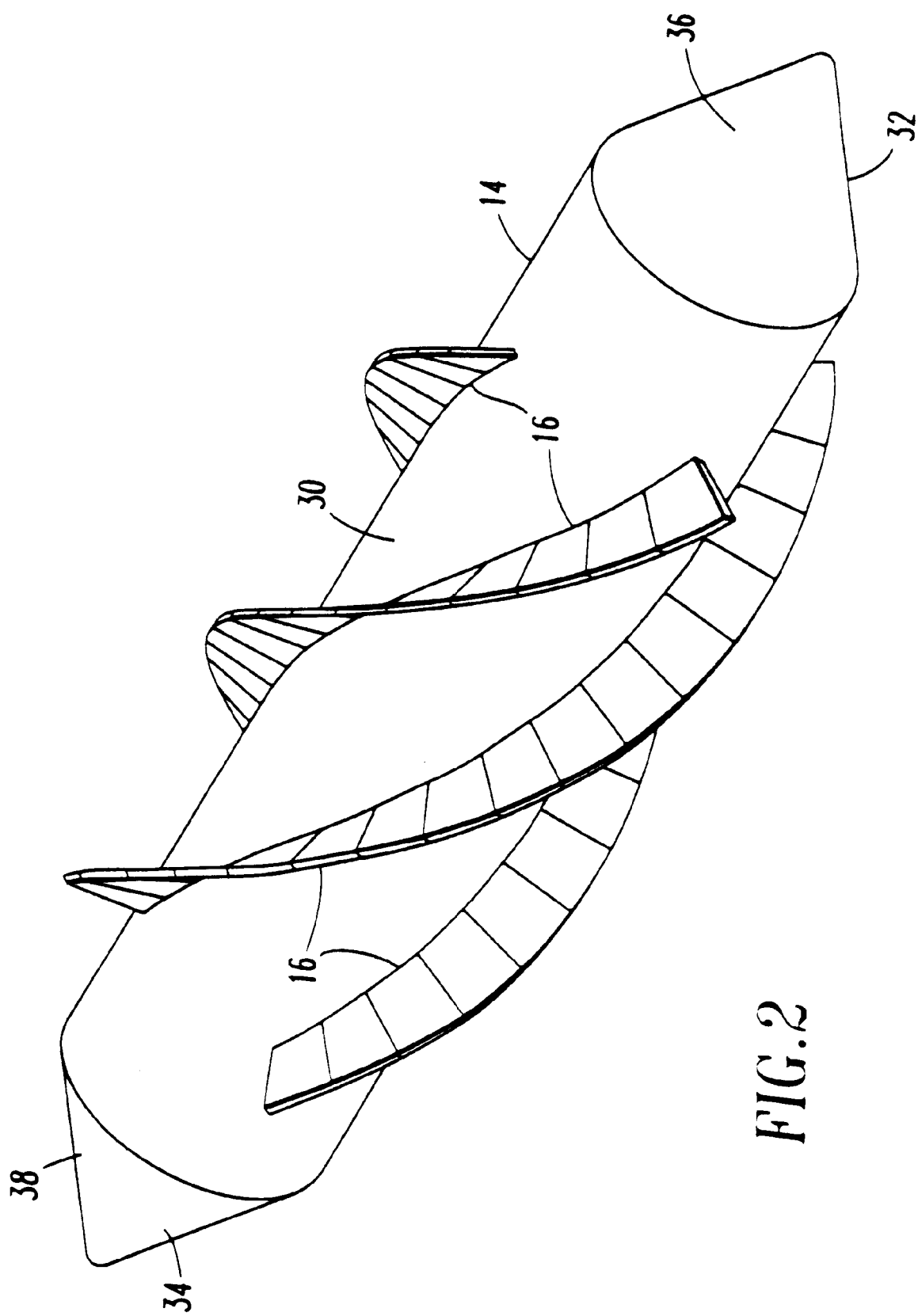
FIG. 2 is a perspective view of the impeller of the rotary fluid pump shown in FIG. 1.

Although this invention is suitable for other uses, it will be described as being used as a rotary blood pump for insertion into a patient. Such description is for purposes of explanation and is not intended to limit the scope of this invention.

FIGS. 1 through 5 illustrate a present preferred embodiment of the invention substantially comprising an axial rotary pump 10 having a housing 12, an impeller 14 with impeller blades 16, a stator member 18, means for levitating the impeller 14 within the housing 12 at a centered position and means for rotating the impeller 14. The housing 12 is preferably cylindrical and has an internal surface 20, an external surface 22 concentrically spaced from the internal surface 20, an inlet 24 and an outlet 26. The internal surface 20 defines an internal region 28 in which the impeller 14 is positioned. The impeller 14 (FIG. 2) has a substantially axially symmetric elongated body 30, a conical-shaped nose 32 and a conical-shaped tail 34. Magnetic targets 36 and 38 are positioned over the impeller nose 32 and the impeller tail 34, respectively. The impeller blades 16 are substantially helical soft magnetic material and are attached to permanent magnets 13 on the body of the impeller 14.

The stator member 18 has an upstream set of stationary blades 40, a downstream set of stationary blades 42, a motor stator 44 and an angle sensor 40. The upstream set of stationary blades 40 and the downstream set of stationary blades 42 are attached to the housing 12 and converge toward the longitudinal axis 48 of the housing 12, wherein the free ends of the upstream set of stationary blades 40 and the free ends of the downstream set of stationary blades 42 define an upstream passageway 50 and a downstream passageway 52, respectively. The impeller nose 32 and the impeller tail 34 extend within the upstream passageway 50 and downstream passageway 52 respectively, such that gaps 54 and 56 are formed between the free ends of the upstream and downstream sets of the stationary blades 40 and 42 and the impeller nose 32 and the impeller tail 34, respectively. As can be best seen in FIG. 4, the downstream set of stationary blades 42 further defines fluid flow regions 58 within the internal region 28 of the housing 12. Although not shown, similar fluid flow regions are defined by the upstream set of stationary blades 40. The upstream and the downstream sets of stationary blades 40 and 42 are preferably made from soft magnetic material; however, they can be made from permanent magnets located in series. Although four stationary blades are shown comprising each set of the upstream and downstream sets of stationary blades 40 and 42, other combination of blades can be used.

The means for rotating the impeller is a brushless DC motor having a motor stator 44, angle sensor 46, a impeller elongated body 30 having permanent magnets 13, flux focusing structures 15 made from soft magnetic material, and impeller blades 16 which serve as the motor poles and are made from soft magnetic material coated with biocompatible material. The motor stator 44 and the angle sensor 46 are positioned within the housing 12 between the internal surface 20 and the external surface 22. Motor stator coils 66 are wound on the motor stator 44. The control of the motor stator coil currents to affect the desired speed in the impeller can be accomplished by conventional means. Although this is the preferred means for rotating the impeller, a variety of other rotation means can be used in the invention. Alternatively, the brushless D.C. motor can take the form of a two pole motor.

The means for levitating (FIG. 4) the impeller 14 is a conical bearing which includes independently controlled coils 60 wound around the backiron segments 62 made from soft magnetic material, segmented and radially magnetized permanent magnets 64 and four stationary blades 42 which act as pole pieces. The coils 60 are controlled to center the impeller 14 between the stationary blades 42. This design is particularly suited for use where fluid flow is required through the four fluid flow regions 58. The levitation means depicts an active radial bearing.

This conical bearing provides radial stiffness and axial stiffness when it is controlled with a feedback system and amplifier. Electromagnetic coils 60 wound around the backiron segments 62 direct the magnetic flux from the electromagnetic coils 60 such that the impeller tail 34 is suspended and substantially centered within the downstream passageway 52. Further, permanent magnets 64 are provided within the backiron segments 62 in order to provide a permanent bias thus, reducing the steady state current. By winding electromagnetic coils 60 around the backiron segments 62, rather than around the downstream set of stationary blades 42, the fluid flow regions 58 remain large enough for blood to pass therethrough without forming regions of stagnant or turbulent flow.

Position sensors 65 are attached to the inlet 24 and the outlet 26 of the housing 12 and adjacent to the impeller nose 32 and the impeller tail 34. Any position sensor can be used including a hall-effect, eddy-current, or infrared optical sensors. The impeller 14 position can even be sensed from changes in inductances of the coils 60. Magnetic bearings controlled with such a sensing scheme are referred to as sensorless bearings when used in conjunction with bearings as described in "Analysis of Self-Sensing Active Magnetic Bearings Working On Inductance Measurement Principle," D. Vischer et al., Second International Conference on Magnetic Bearings, Tokyo, pp. 301–309, July 1990.

Figure 5:
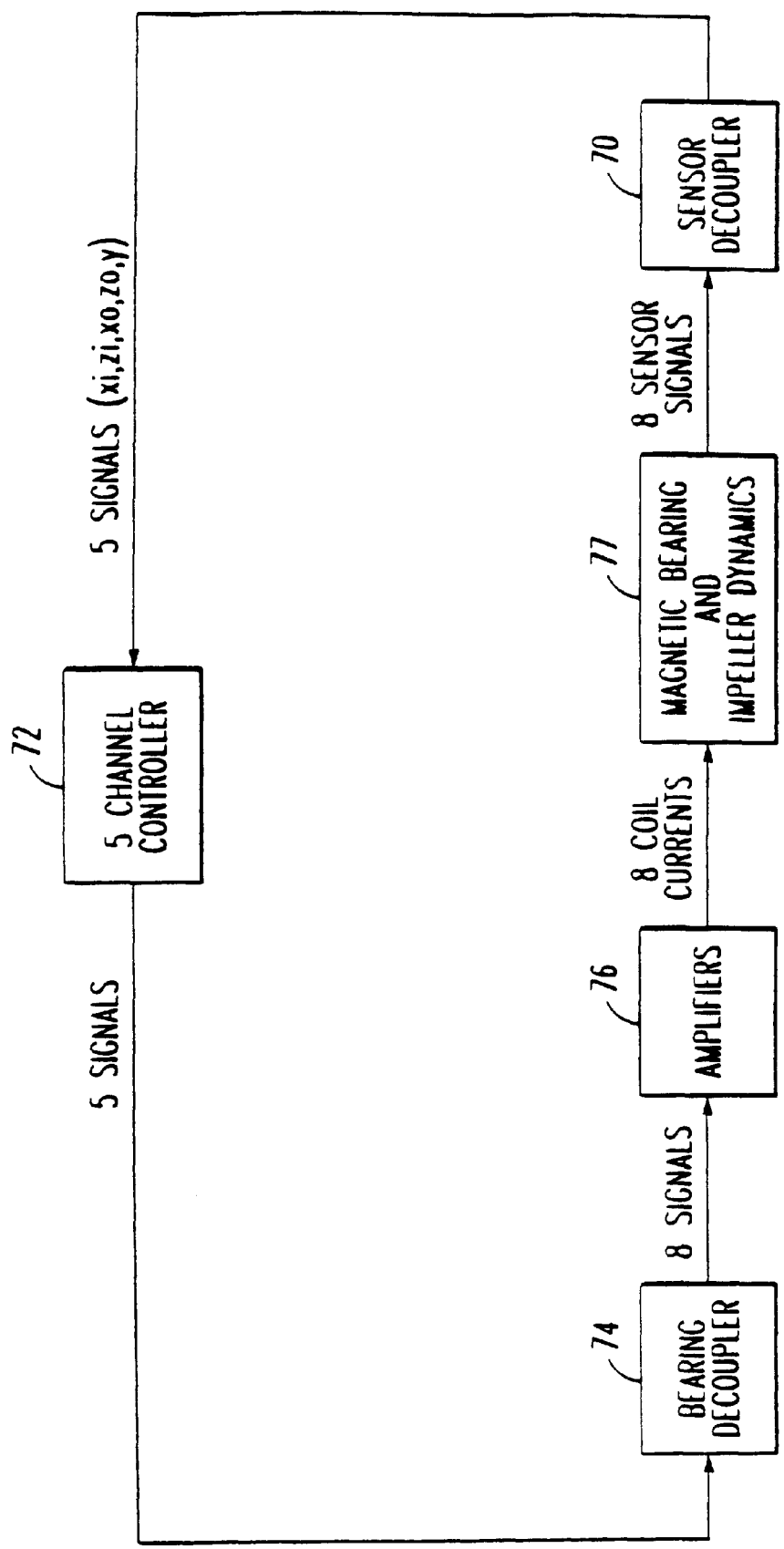
FIG. 5 is a schematic diagram of the magnetic bearing control used in the rotary fluid pump shown in FIG. 1.

In order to magnetically levitate the impeller 14 a feedback controller is used as diagramed in FIG. 5. Position errors are measured with 8 position sensors 65 and transformed into the error signals $x_i$, $z_i$, $O$, $z_o$ and y, while $x_i$ and $z_i$ measurements correspond to the x and z impeller displacement of the impeller measured at the inlet 24 and $x_o$ and $z_o$ are measured at the outlet 26. The error transformation is accomplished with the sensor decoupler 70 shown in FIG. 5 which is simply a matrix multiplication accounting for the position and orientation of the sensors 65. The five principle displacement errors are filtered independently with the five-channel controller 72 which outputs five desired restoring forces to be applied to the impeller 14. The bearing decoupler 74 transforms these commands via a matrix multiplication into an appropriate coil current pattern to be applied to the coils 60. The current commands are input to an amplifier 76 which drives the coils 60. The principle of decoupling is well-known, as are various kinds of controls used in the five channel controller. Some examples of control algorithms are proportional-integral-derivative and zero-power control. The magnetic bearing sensors and impeller dynamics 77 models how the bearing fluxes react to the coil currents and how the impeller responds to the magnetic forces created by the bearing fluxes.

During operation of the rotary pump 10, the blood enters the inlet 24 of the housing 12 in the direction of arrow A. The blood passes over the impeller nose 32 through the gap 54 and the fluid regions 58. The upstream set of stationary blades 40 serve to straighten the incoming blood flow. The impeller 14 is rotated by the rotating means and the impeller blades 16 accelerate and impart energy to the blood such that the blood moves through the housing 12 toward the outlet 26. The downstream set of stationary blades 42 function to recover velocity energy as pressure energy from the blood flow exiting the impeller blades 16. Before exiting the housing 12, the blood flow passes through the gap 56 and the fluid flow regions 58 formed by the downstream set of stationary blades 42. The gaps 54 and 56 are sized and proportioned such that they are large enough to prevent regions of stagnation and excessive shear from forming while being small enough to provide efficient magnetic suspension of the impeller 14. Furthermore, the axially symmetric configuration of the impeller elongated body 30 provides for blood to flow through the housing 12 without creating regions of stagnation or excessive shear.

As noted above, the impeller nose 32 and the impeller tail 34 are magnetically suspended and centered within the housing 12 by the magnetic flux created by the electromagnetic coils 60 and directed through the upstream and downstream sets of stationary blades 40 and 42. The gaps 54 and 56 are small enough to allow for the magnetic flux to be directed across the gaps without a substantial increase in the magnetic circuit reluctance. If during pumping of the blood, the impeller 14 moves from its centered position within the housing 12, position sensors 65 will detect this movement and the means for levitating the impeller 14 will apply a net force and moment to the impeller 14 to reposition the impeller 14 to its centered position within the housing 12.

For example, a net force in the y direction is accomplished by increasing the flux in the outlet gap 56 with appropriate corresponding coil currents. The calculation of the currents is accomplished with the sensor decoupler 70, the five channel controller 72, and the bearing decoupler 74 working in combination. Alternatively, the sensing of the movement of the impeller 14 can be accomplished by estimating the coil inductances from the coil voltages and currents and then calculating the gap from the coil inductances.

The variation of magnetic components which include both electric motors and magnetic bearings is extensive and well-documented. Below are described some typical magnetic components and how some of these magnetic components can be used in embodiments of the present preferred invention.

Figure 6:
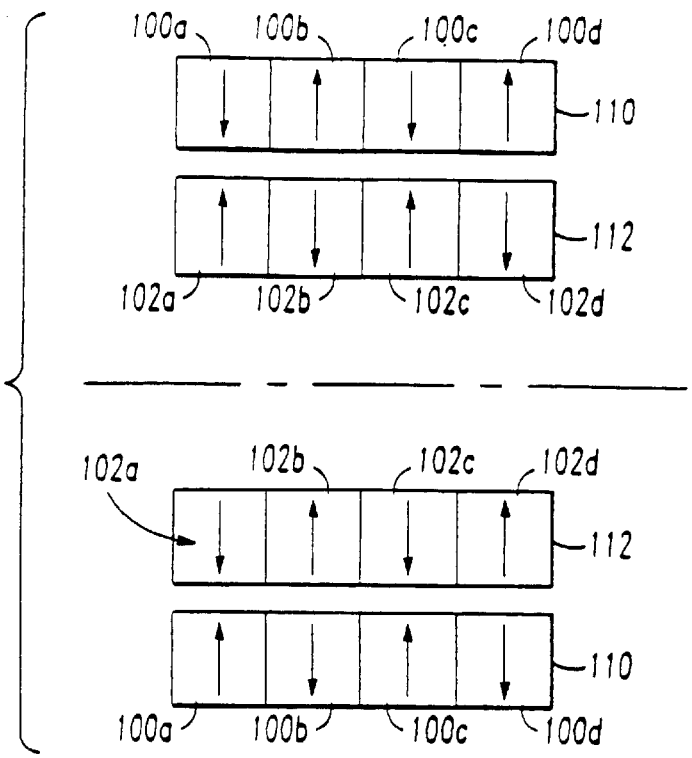
FIG. 6 is a schematic view of a passive radial bearing which is a permanent magnet bearing.

Passive Radial Bearing (PRB): FIG. 6 shows a common design of a passive radial bearing (PRB) which is a permanent magnet bearing. It consists of alternatively magnetized annular permanent magnets 100a, 100b, 100c 100d, 102a, 102b, 102c and 102d comprising two annular magnet rings 110 and 112, respectively, of the passive radial bearing. Either annular ring 112 or 110 can serve as either the impeller or the stator of a rotary pump.

Figure 7:
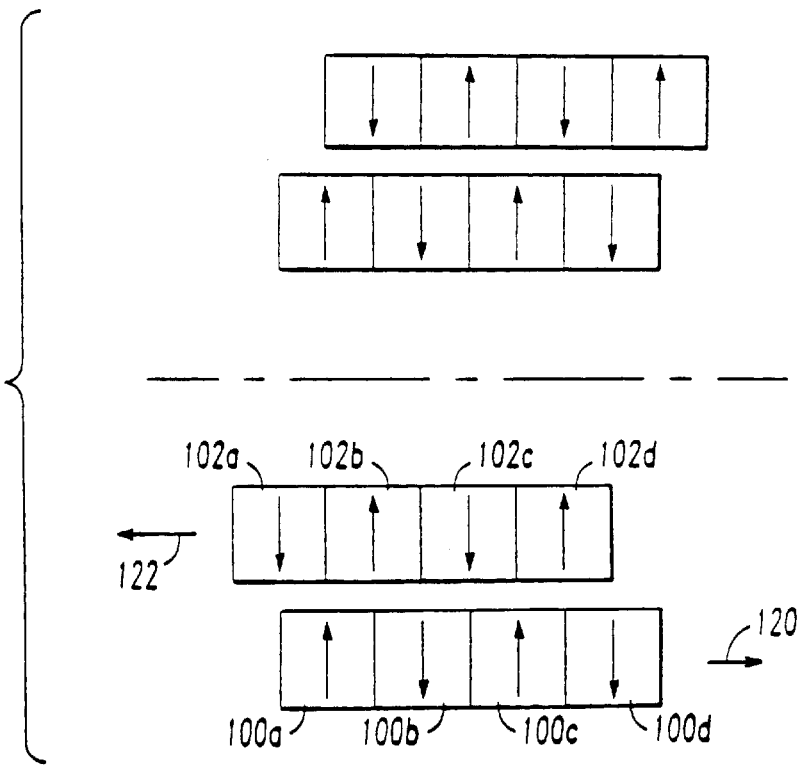
FIG. 7 is a schematic view of the passive radial bearing of FIG. 6 having an axial offset.

The annular magnet rings 110 and 112 are magnetized to provide radial stiffness. However, it is a property of this type of bearing that the axial stiffness is negative with a magnitude equal to twice the radial stiffness. Although this negative stiffness cannot be used alone for axial positioning, it can be used to provide axial bias forces as shown in FIG. 7. By axially shifting the annular magnet rings 110 and 112 relative to each other net steady state forces 120 and 122 can be applied in the axial direction as shown by the arrows. This is due to the fact that magnet 102a is applying a force on magnet 100a in the direction 120, and magnet 102b is applying a force on magnet 100a in the direction 120. Similar interaction occur amongst the other magnets. Passive radial bearings are further described in "Stacked Structures of Passive Magnetic Bearings" J. P. Yonnet et al., Journal of Applied Physics, vol. 70, no. 10, pp. 6633–6635.

Figure 8:
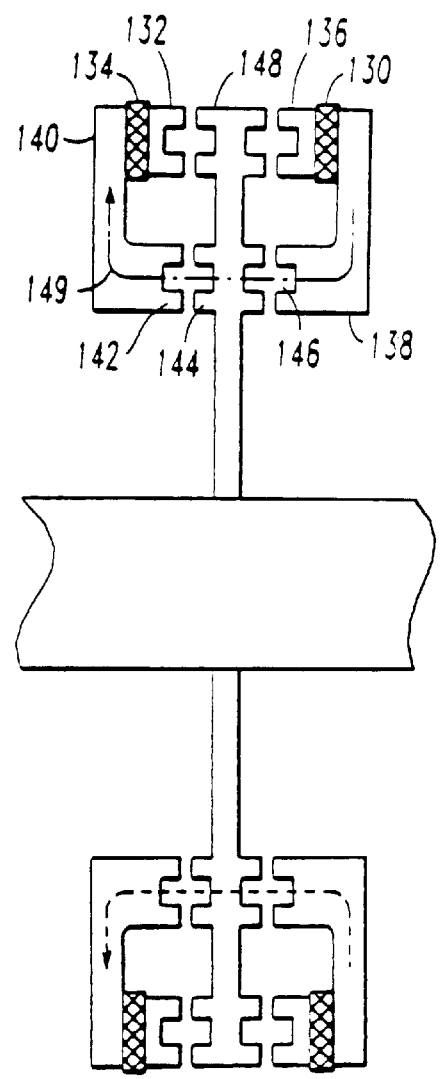
FIG. 8 is a cross-sectional view of a passive radial bearing where the pole pieces are notched to provide pole saliency.

Another kind of PRB is shown in FIG. 8. This bearing has a stator which includes stator magnets 130 and 134, soft magnetic stator pole pieces 132, 136, 138, and 140. The bearing impeller 148 is a soft magnetic material with teeth 144. Permanent magnets 130 and 134 are magnetized axially so that a magnetic flux passes through pole pieces 132, 136, 138, and 140 and through the bearing impeller 148 in a closed loop as shown by arrow 149. The impeller teeth 144 and the stator teeth 142 consisting of the stator magnets 130 and 134 and stator pole pieces 132, 136, 138, and 140 tend to align to minimize the reluctance of the magnetic circuit which results in the radial position of this bearing. This passive radial bearing is unstable in the axial direction as is the bearing of FIG. 6. By mounting the impeller 148 to the pump housing and the stator to the impeller 148 we can interchange stator and impeller 148 of this bearing. The recesses 146 defined by teeth 142 may be filled with nonmagnetic material to eliminate blood stagnation zones.

Figure 9:
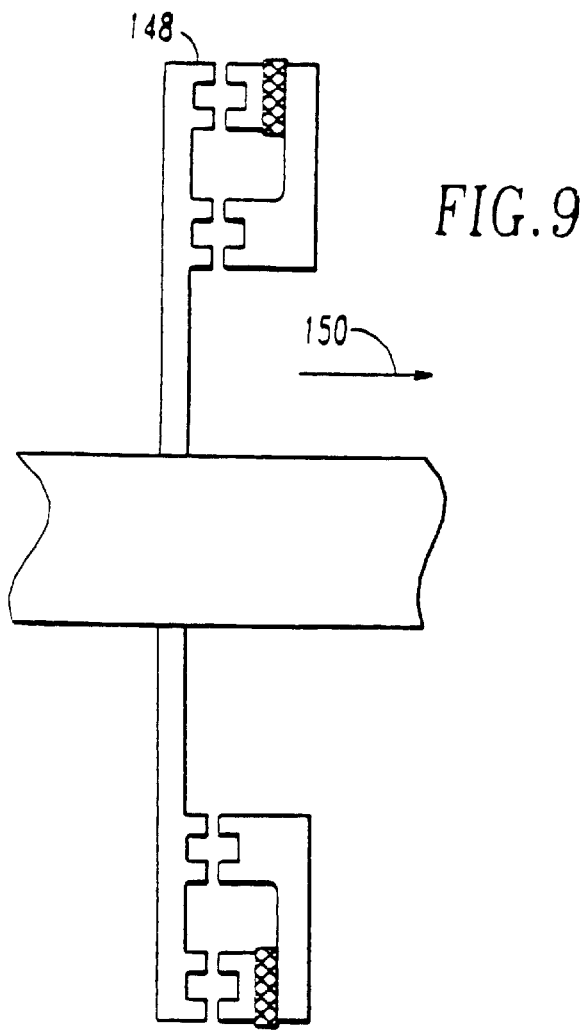
FIG. 9 is a cross-sectional view of another salient type passive radial bearing having a thrust bias which is equivalent to a passive radial bearing with axial offset.

FIG. 9 illustrates a passive radial half bearing (PRB2). This bearing is similar to that of FIG. 8 in that it provides radial position to the impeller 148, but unlike the PRB of FIG. 8 it provides a bias force on the impeller 148 in the direction 150.

Figure 10A:
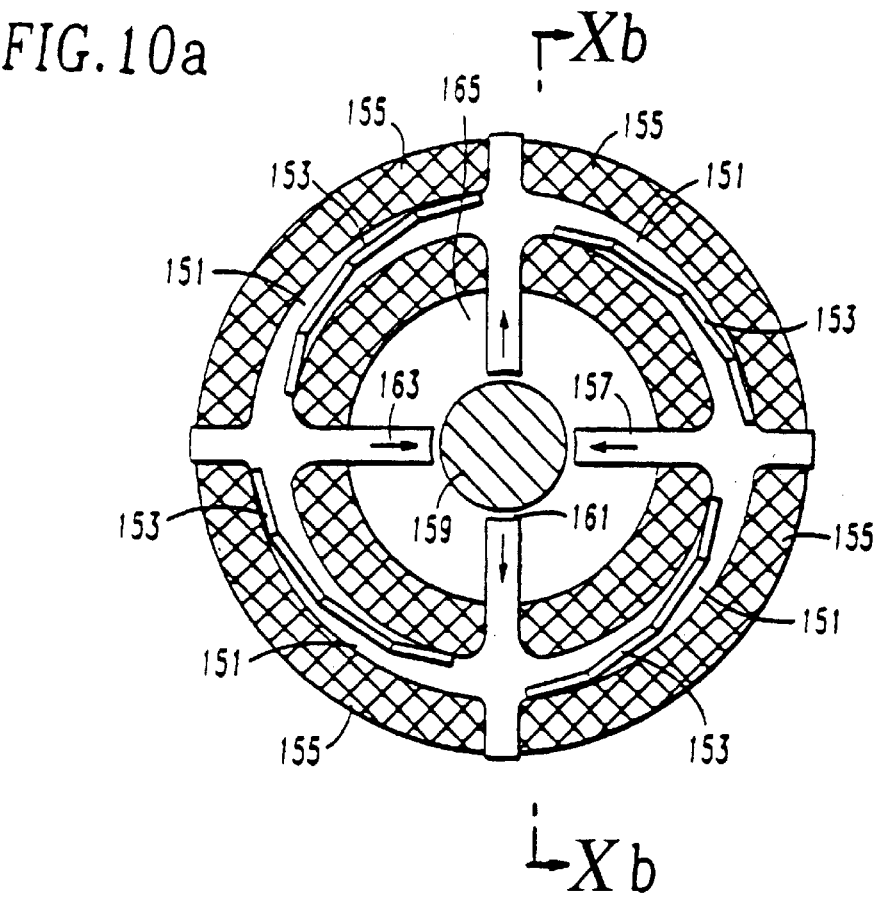
FIG. 10a is a cross-sectional view of an active radial bearing with large fluid flow regions.
Figure 10B:
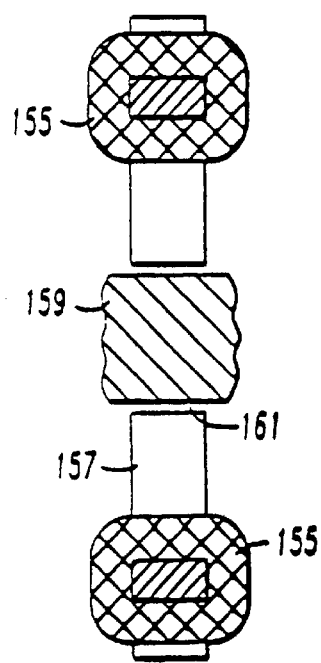
FIG. 10b is a cross-sectional view of the active radial bearing of FIG. 10a taken along line Xb—Xb.

Active Radial Bearing (ARB): FIGS. 10a and 10b depict an active radial bearing (ARB) The bearing stator consists of soft magnetic material backiron segments 151, segmented and radially magnetized permanent magnets 153, independently controlled coils 155 and four pole pieces 157. The rotor is soft magnetic material 159. The permanent magnet provide a bias flux in the four gaps 161 between the rotor and the stator. The direction of this bias is shown with the four arrows 163. The stator coils are controlled to center the rotor in the stator. This design is particularly suited for use in where fluid flow is required through the four bearing passages 165.

This bearing provides radial stiffness and essentially little axial stiffness when it is controlled with a feedback system and amplifier.

Figure 11:
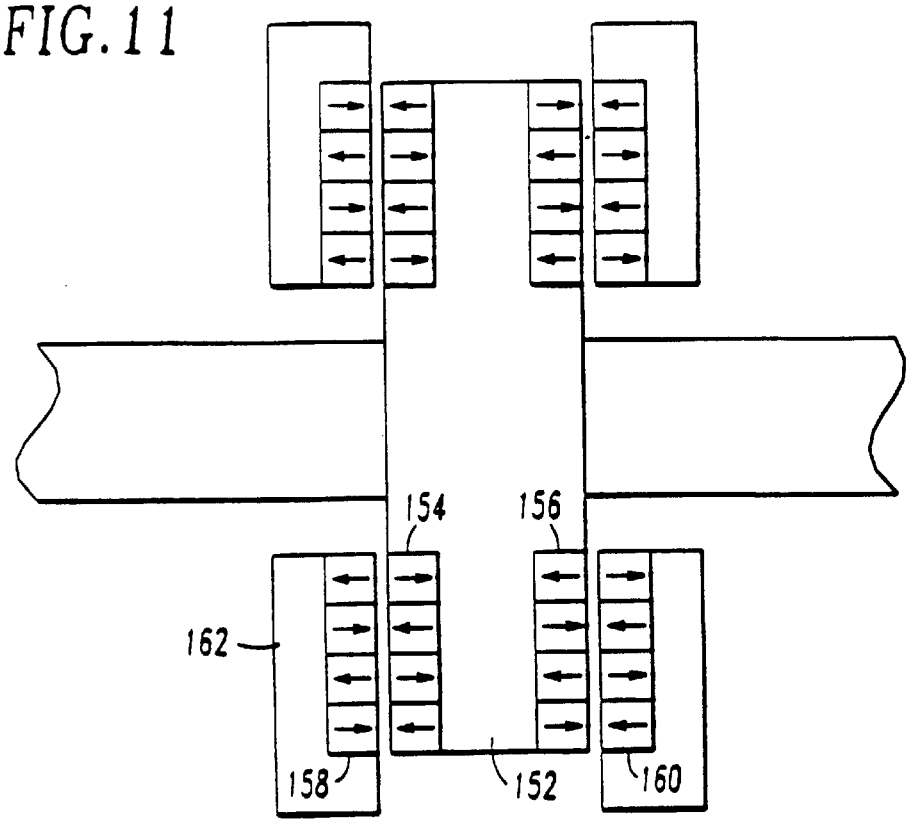
FIG. 11 is another view of a passive thrust bearing.

Passive Thrust Bearing (PTB) and Passive Thrust Half Bearing (PTB2): FIG. 11 illustrates a passive thrust bearing. The bearing impeller 152 supports two magnet stacks 154 and 156 which repel magnet stacks 158 and 160 on the stator 162. The net effect of the magnetic interaction is that the bearing has a positive axial stiffness and negative radial stiffness.

Figure 12:
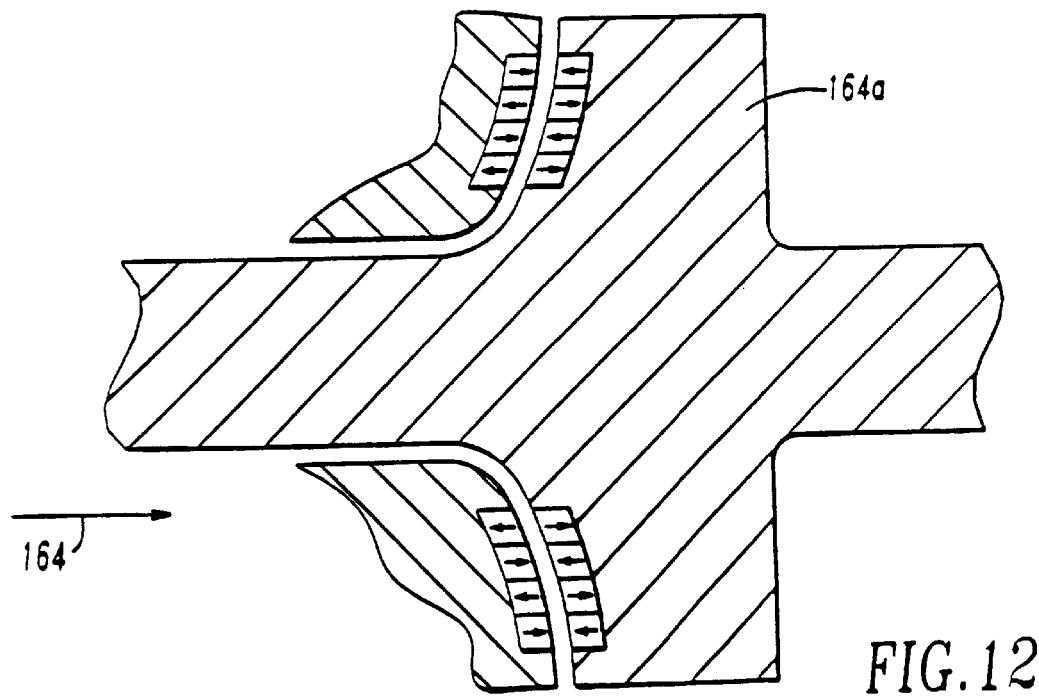
FIG. 12 is a cross-sectional view of a half-passive thrust half bearing wherein the two components are contoured to compound one another.

A similar bearing is shown in FIG. 12 which only applies thrust to the rotor in the direction 164. Such a bearing is called a passive thrust half bearing (PTB2). All bearing gaps can be contoured to provide for blood flow without stagnant and turbulent flow.

Figure 13:
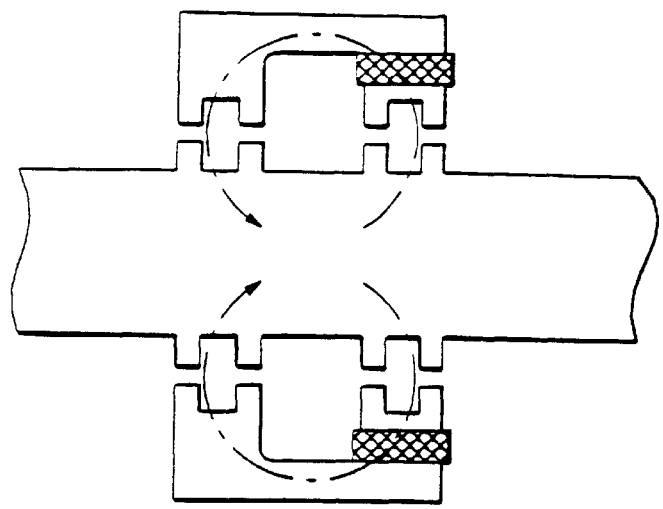
FIG. 13 is another passive thrust: bearing where pole pieces are notched to provide pole saliency.

FIG. 13 shows a thrust bearing which uses the same principles as the radial bearing of FIG. 8 but is distinguished from FIG. 8 in that the axial gaps of FIG. 8 are reoriented radial gaps in FIG. 13.

Figure 14:
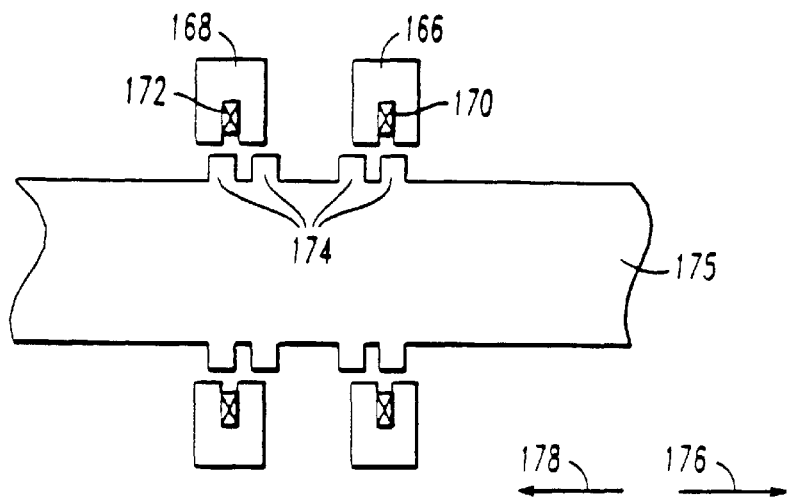
FIG. 14 is another active thrust bearing.
Figure 15:
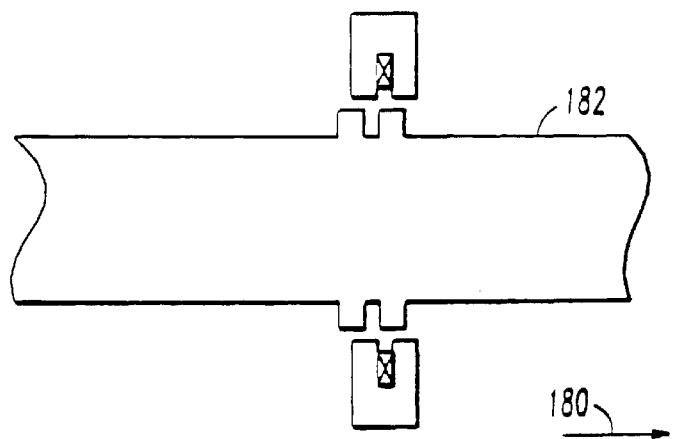
FIG. 15 is half-active thrust half bearing.

Active Thrust Bearing (ATB) and Active Thrust Half Bearing (ATB2): FIG. 14 depicts an active thrust bearing. The stator consists of pole pieces 166 and 168 and coils 170 and 172 which are driven independently. Applying a current to coil 170 causes the stator pole piece 166 to line up with impeller teeth 174 by applying a force on the impeller 175 in the direction 176. Similarly, energizing coil 172 applies a force on the impeller 175 in the direction 178. By sensing the axial position of the impeller 175, feedback controls can position the impeller 175 axially. These bearings do have some negative radial stiffness. FIG. 15 shows an active thrust half bearing (ATB2) which only applies force in the direction 180 to the impeller 182.

Figures 16, 17:
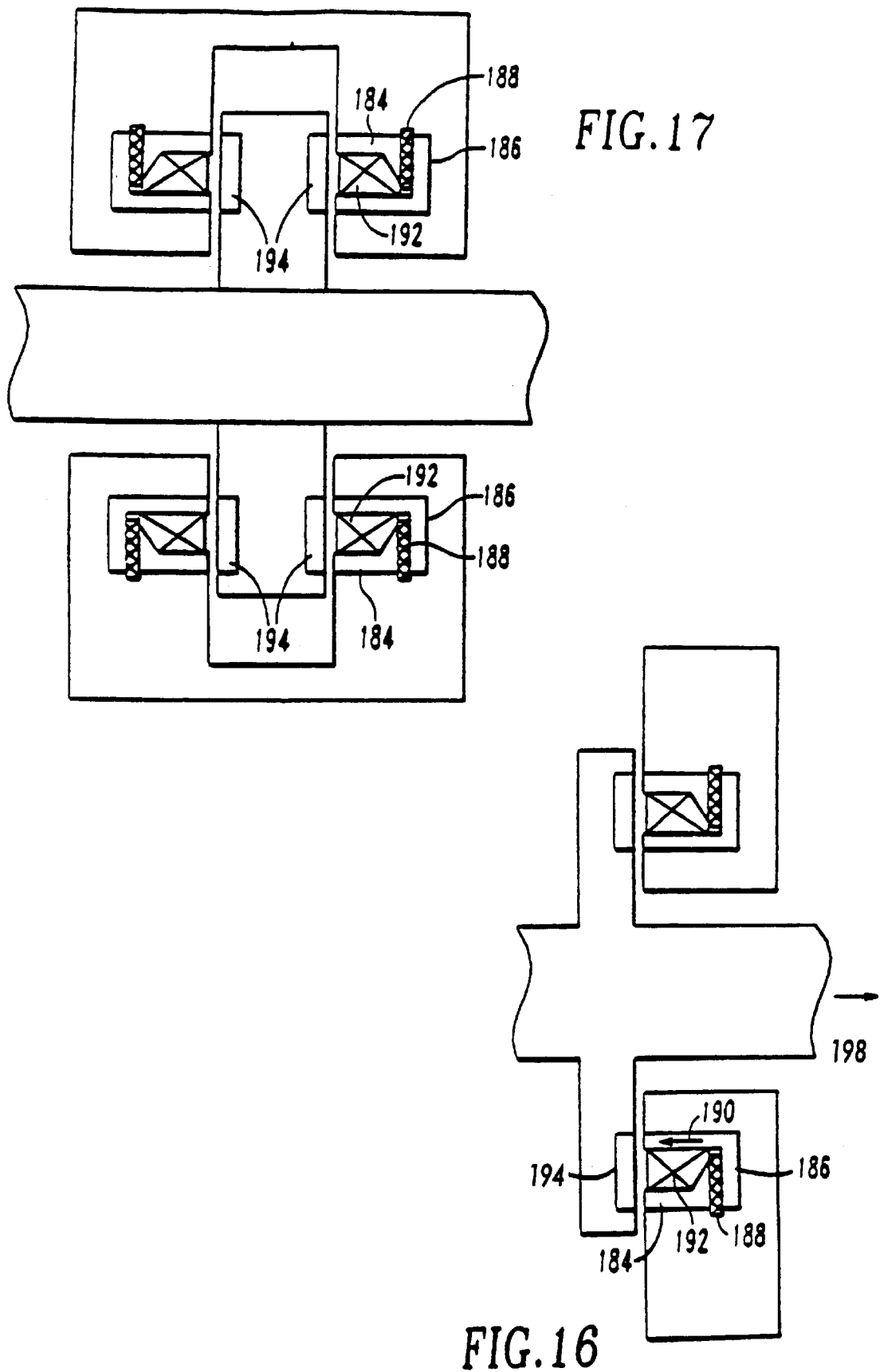
FIG. 16 is another half-active thrust half bearing.
FIG. 17 is active thrust bearing.

FIG. 16 illustrates an active thrust half bearing. The stator consists of soft magnetic pole pieces 184 and 186 driven by a permanent biasing magnet 188 in the direction 190. The bias flux is modulated by the control coil 192 so that the force applied to the soft magnetic target 194 is controlled. This is an ATB2 because force is applied to the impeller only in the direction 198. FIG. 17 shows an ATB comprised of two ATB2's which is based on the same principles as FIG. 16.

Figure 18:
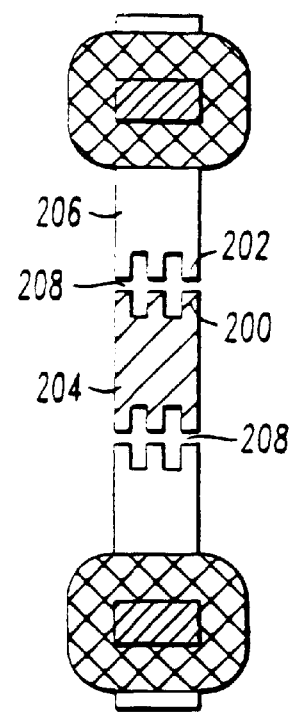
FIG. 18 is a hybrid of an active radial bearing and a passive thrust bearing.

Hybrid Components: It is often possible to physically integrate the function of two magnetic components. For example, FIG. 18 shows the ARB of FIGS. 10a and 10b with teeth 200 and 202 added to the impeller 204 and stator 206, respectively. The magnetic field across the gap 208 of the bearing cause the teeth 200 and 202 to align passively without feedback control hence this is a hybrid of a PTB and an ARB which is denoted as "PTB=ARB."

Figure 19:
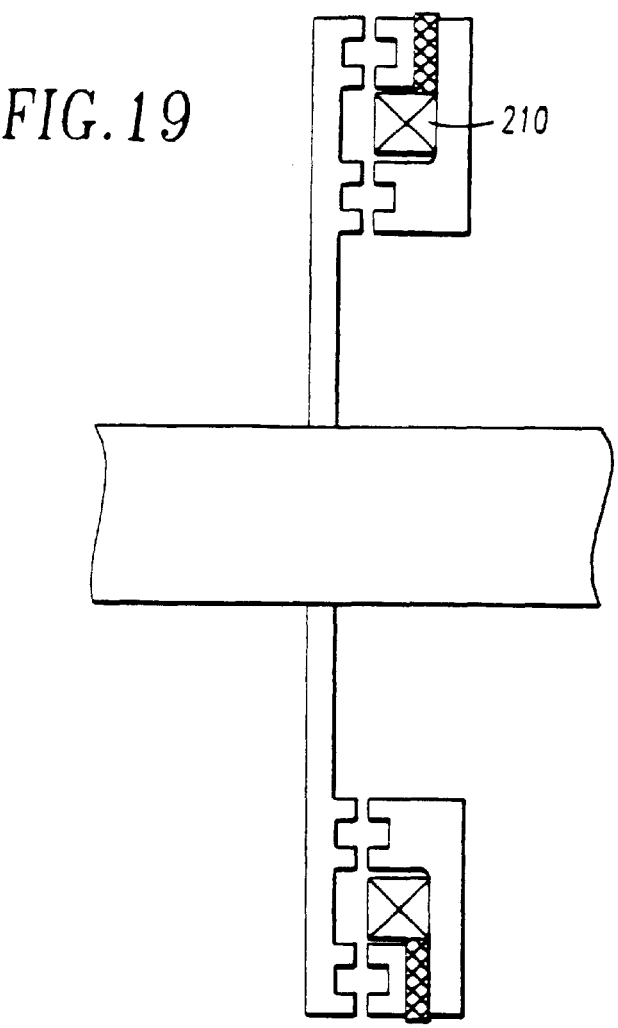
FIG. 19 is a hybrid of a half-active thrust half bearing and a passive radial bearing.

A similar hybrid is shown in FIG. 19. Coil 210 is added to a PRB which is half the PRB of FIG. 9. This coil actively controls thrust in one direction along the impeller axis. Because the function of an ATB2 is added to a PRB, the resulting hybrid is denoted as "ATB=PRB."

The inlet conical bearing in FIG. 1 is a hybrid of an active radial bearing and an active thrust half-bearing because the pole face angles are intermediate between a thrust bearing and a radial bearing. The poles of the conical bearing also serve as pump stator blades.

Hybridization of fluid and magnetic components is also possible. Pump blades, both impeller and stator blades, can be used as magnetic flux paths. The stator blades in FIG. 1 act as magnetic poles for the conical magnetic bearings. Furthermore, the impeller blades are flux paths for the brushless DC motor in FIG. 1. It is also possible for stator blades to serve as supports for passive magnetic bearing stators, and for impeller blades to support magnetic structures.

Figure 20:
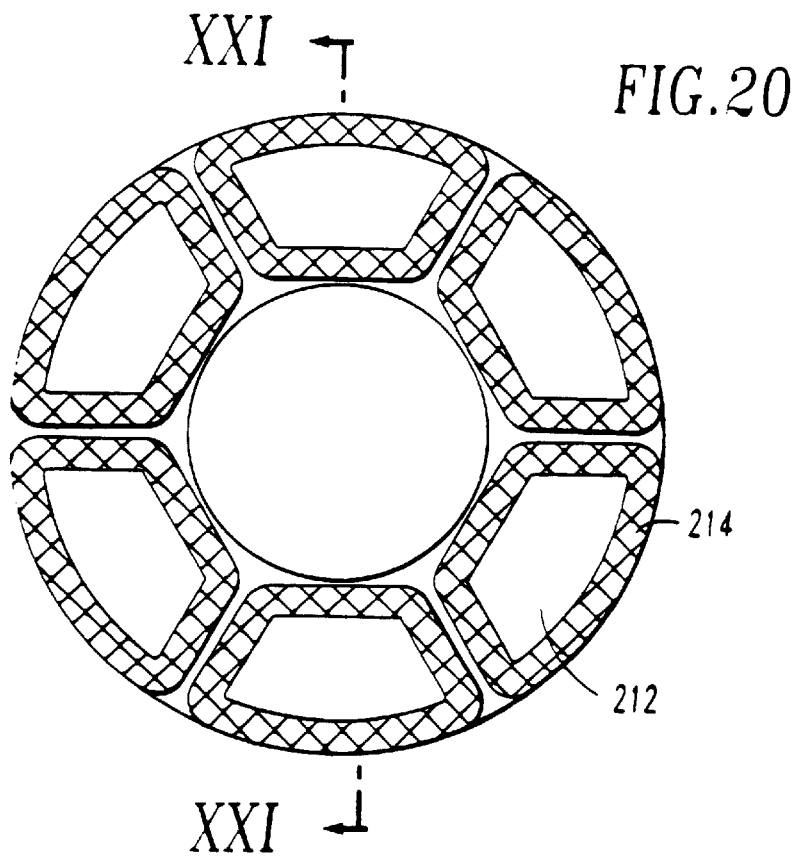
FIG. 20 is a hybrid of stator of an induction motor and an active half thrust bearing.
Figure 21:
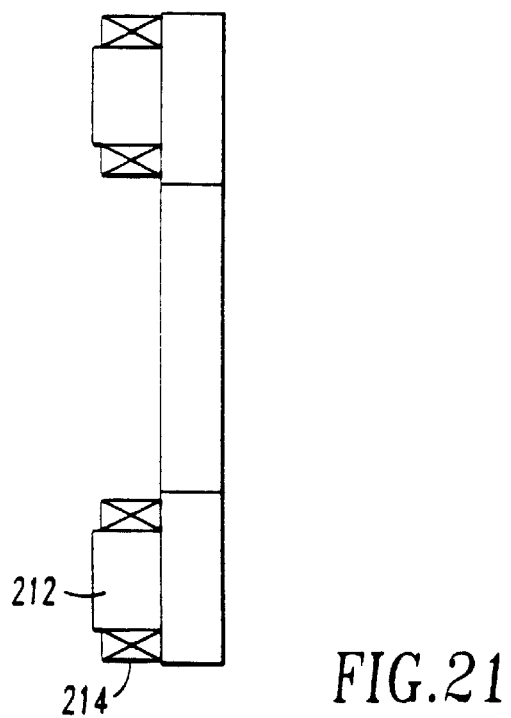
FIG. 21 is a cross-section of the stator shown in FIG. 20 taken along the line XXI—XXI.
Figure 22:
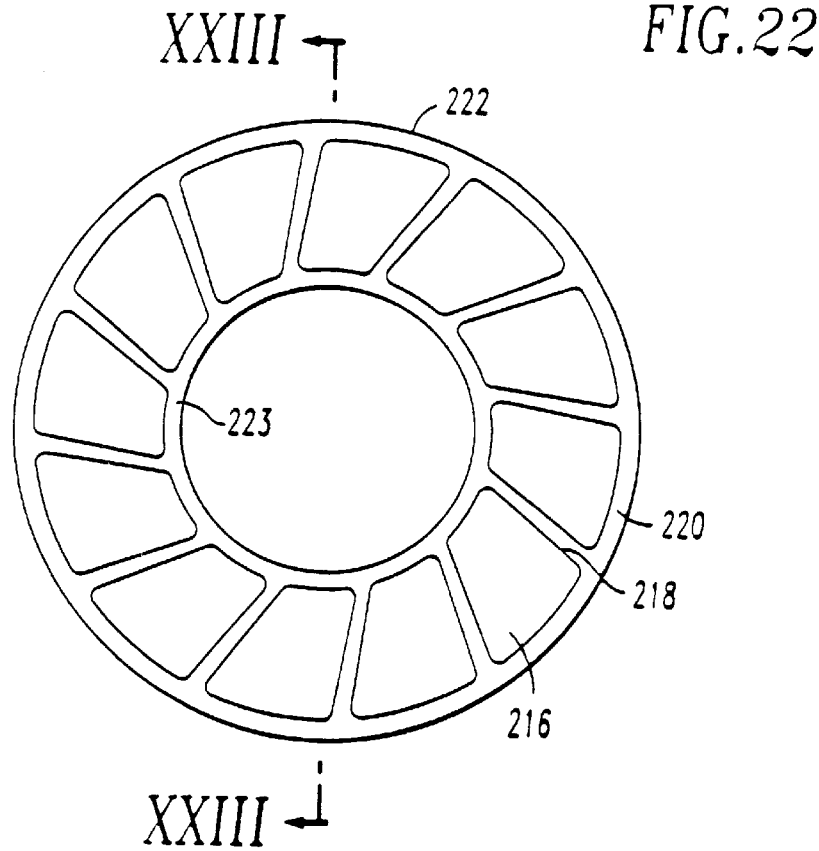
FIG. 22 is an armature of a hybrid of an induction motor and an active half thrust bearing.
Figure 23:
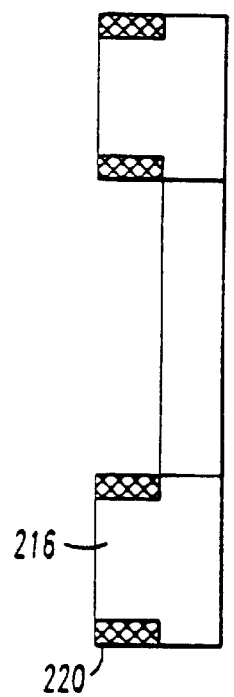
FIG. 23 is a cross-section of the armature shown in FIG. 22 taken along line XXIII—XXIII.

FIGS. 20 through 23 illustrate a pancake induction motor which can be controlled for thrust as well. FIGS. 20 and 21 show a stator with stator poles 212 and stator coils 214. FIGS. 22 and 23 show an armature 222 with magnetic iron members 216 and slot conductors 218. Annular regions 220 and 222 are also conductors. By controlling the six stator coil currents it is possible to simultaneously vary the motor torque and thrust force across the pancake motor. This can be done by varying the rotational frequency of the stator field and the amplitude of the stator field independently. Similar hybridization of a variable reluctance type motor is described in U.S. Pat. No. 4,683,391.

An alternative embodiment of the motor to be used as rotation means is the two pole type brushless DC motor shown in FIG. 24. The rotor 224 is shwon in FIG. 24 along with the stator.

Alternative Means of Rotation: An alternative motor configuration for FIG. 1 is shown in FIG. 25. This is a variable reluctance type motor where the rotor poles and the impeller blades are hybridized. The rotor 224 is made from soft magnetic material as are the blades 226. The commutation for this motor is different from that for the DC brushless motor, but well known to those skilled in the art of motor control.

Figure 26:
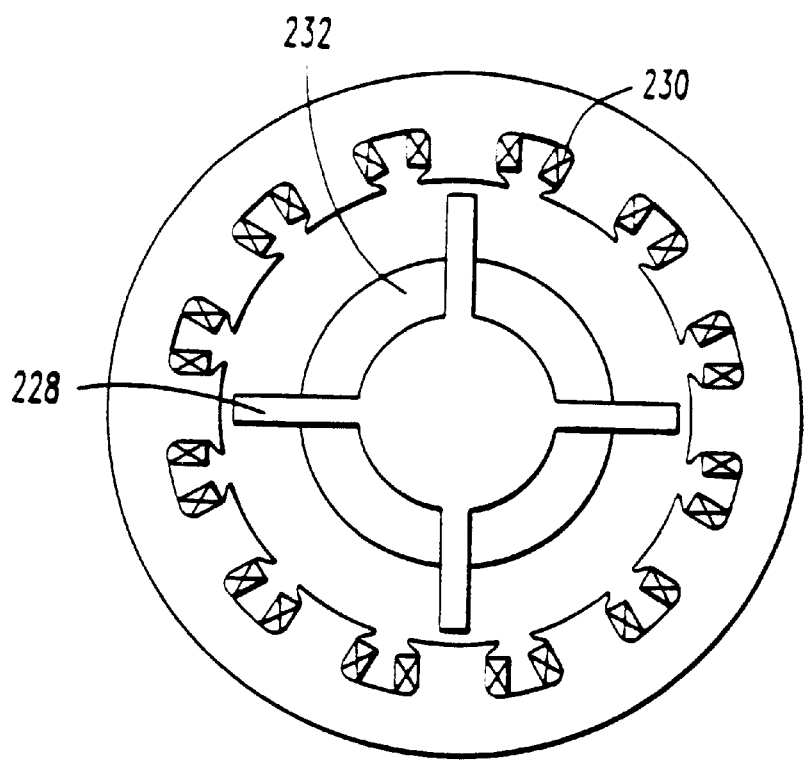
FIG. 26 is a cross-sectional view of an induction motor hybridized with impeller blades.

FIG. 26 is yet another possible motor configuration to be used in the rotary pump shown in FIG. 1. It is an induction motor whose impeller slot structure is hybridized with the impeller blades 228. By applying a rotating magnetic field to the impeller via the stator coils 230, currents are induced in the slot conductors 232 which are current return paths connecting adjacent slots conductors not shown, but existing on the axial end caps of the impeller.

Figure 27:
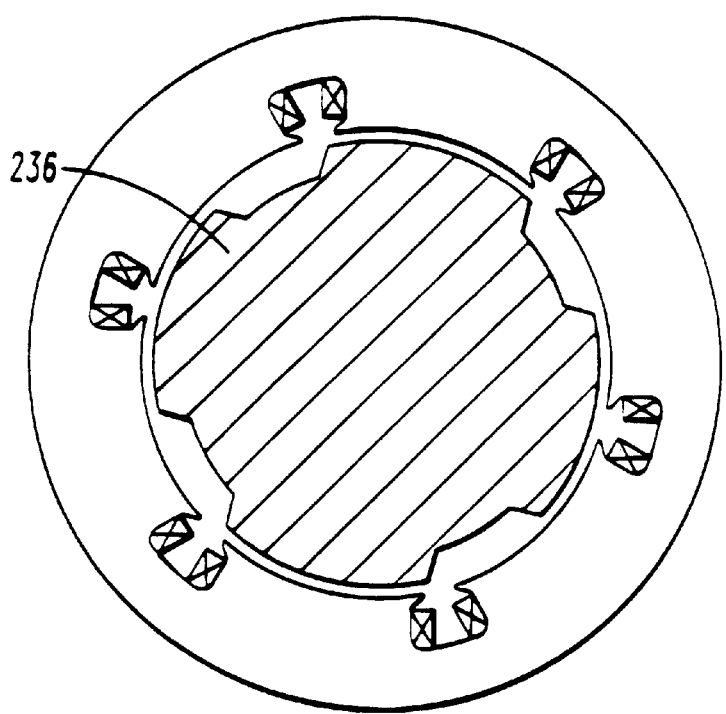
FIG. 27 is a cross-sectional view of another variable reluctance motor.

FIG. 27 depicts a variable reluctance motor cross section to be used in the rotary pump of the present preferred invention. The impeller of this motor 236 is made from soft magnetic material (e.g. approximately 3% silicon-iron).

Figure 28:
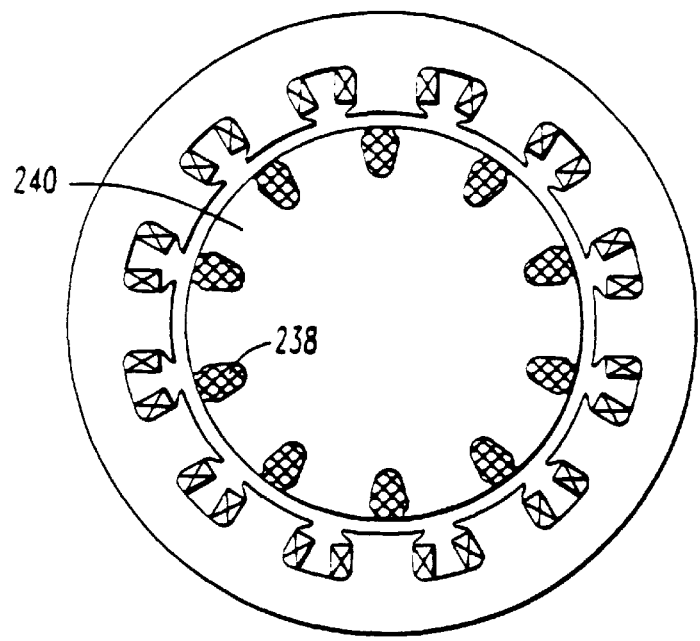
FIG. 28 is a cross-sectional view of another an induction motor.

FIG. 28 is an induction motor. The cross-section of the motor depicts slot conductors 238 and a soft magnetic material impeller 240. Slot conductor end-turn current paths are not shown.

The following acronyms can be utilized to describe various configurations for the rotation means and the levitation means of the present preferred invention.

| Pump Type Descriptors | |
|---|---|
| FH | fixed hub |
| RH | rotating hub |
| AO | axial outlet |
| RO | Radial outlet |
| Sp | fixed-hub support |
| sb | stator blade |
| ib | impeller blade |

| -continued | |
|---|---|
| Magnetic Components | |
| ARB | active radial bearing |
| ATB | active thrust bearing |
| ATB2 | active thrust half-bearing |
| PRB | passive radial bearing |
| PRB2 | passive thrust half bearing |
| VRM | variable reluctance motor |
| DCBM | direct current brushless motor |
| IM | induction motor |
| Other Notations | |
| X | is used to indicate a magnetic component X, where the magnetic gap is positioned adjacent the housing. |
| $\underline{X}$ | is used to indicate a magnetic component X, where the magnetic gap is adjacent the hub. |
| X ‖ ib | is used to indicate that the component X is hybridized with impeller blades. |
| X ‖ sb | is used to indicate that the component X is hybridized with stator blades. |
| — | a line segment indicates that two components are consecutive along the blood flow path. |
| X \| Y | indicates components X and Y are aligned for structural support. |
| = | an equal sign indicated that two components are functionally integrated or "hybridized". |
| (RH,AO) | parenthetical acronyms denote the design type. In this case "rotating hub with axial outlet." |

With these notations we can represent the pump in FIG. 1 by the following formula.

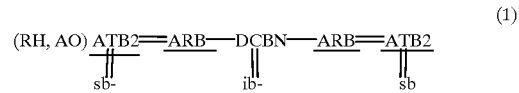

(1)

Each formula consist of a "header" defining the hub type (RH or FH) and the outlet type (AO or RO), followed by an "upper sentence" describing the order and kinds of magnetic components, their gap locations either at the housing or hub and whether or not they are hybridized. Positions of hub supports are also noted in the upper sentence. There is also a "lower sentence" describing the order of fluid components. Vertical alignment between the upper sentence and the lower sentence does not imply any physical alignment unless a "|" is used to indicate alignment or "‖" is used to indicate that components in the two sentences are hybridized.

Formula (1) describes a design which is a rotary hub type (RH) with axial outlet (AO). The components from inlet to outlet along the blood flow path are a stator blade hybridized with an active radial half bearing which forms a conical bearing and the hybridized bearing has its magnetic gap toward the inside diameter of the primary fluid flow path. Reading formula 1 further, a brushless DC motor is hybridized with the impeller blades and has its magnetic gap toward the outside diameter of the fluid flow path. Reading formula 1 further, an active radial bearing is hybridized with an active thrust half bearing which is further hybridized with a set of stator blades.

Using this language many of the embodiments of the rotary pump of the present preferred invention are enumerated. By applying physical constraints, designs are eliminated which are not practical.

A formula header is any one of (FH,AO), (FH,RO), (RH,AO), or (RH,RO). A formula upper sentence is any sequence of magnetic components acronyms and/or support acronyms separated by "–" or "=". The magnetic component acronyms are either underlined or not. The lower sentence is any sequence of impeller blade acronyms or stator blade acronyms. Each acronym in the lower sentence may be aligned with one acronym in the upper sentence provided that order is preserved; that is, if an acronym identifying a magnetic component (A) and an acronym denoting a fluid component (B) are aligned with a "|" or hybridized with "||", and an acronym denoting a magnetic component (C) and an acronym denoting a fluid component (D) are aligned, and if C follows A in the upper sentence we must have D following B in the lower sentence; we call this the "order preserving" property.

Certain formulas can be eliminated because they violate the following simple structural requirements. All formulas with the header (RH,AO) are eliminated due to the existence of a stagnation zone in this configuration. If the bearing is RH type then Sp may not appear in the upper sentence because supports are only needed for the fixed hub (FH) type pump. No two magnetic components may be separated by a support (Sp). If this were to happen the impeller would be divided into two separate pieces. The lower sentence must include at least one impeller blade (ib). If the header contains a fixed hub (FH), then the upper sentence must contain at least one support (Sp). An underlined magnetic component and a non-underlined magnetic component may not be separated with a "=" because magnetic components must have their gaps in the same location, either adjacent the housing or adjacent the hub, in order to be hybridized. The upper sentence must include one motor; however, we may have additional motors to add reliability. The magnetic components must satisfy force/moment balance for x,y,z, pitch ($\theta$) and yaw ($\phi$) motions of the impeller. That is, any bias force associated with PRB offsets or ATB2's must balance.

Collectively the magnetic bearing components, both active and passive must provide positive stiffness (i.e., positive restoring forces to levitation) in the x,y,z, pitch and yaw directions because the motor controls the roll direction. This is characterized mathematically with a positive stiffness matrix, K, relating the five displacements, x,y,z, pitch and yaw, to the corresponding restoring forces and moments. Consider a coordinate frame at the center of mass of the rotor with its axes aligned as shown in FIG. 1. Pitch is rotation about the x-axis; yaw is rotation about the z-axis; and roll is rotation about the y-axis and is controlled by the motor. Let $(\Delta x, \Delta y, \Delta z, \Delta \theta, \Delta \phi)^T$ be the vector of x,y,z pitch and yaw displacements of the impeller relative to the desired levitated position, where superscript "T" denotes transpose. Further, let the vector of corresponding forces and moments measured in the given frame be $(f_x, f_y, f_z, m_{\theta, m100})^T$ and let K be the "support stiffness matrix" of the rotor satisfying $(f_x, f_y, f_z, m_\theta, m_\phi)^T = -K (\Delta x, \Delta y, \Delta z, \Delta \theta, \Delta \phi)^T$.

We require using appropriate feedback control of active magnetic bearings, a particular candidate magnetic bearing configuration having a positive definite symmetric support stiffness matrix. With feedback control this stiffness property can be achieved only over a certain frequency band.

If such a support stiffness matrix is achievable for a particular set and placement of magnetic bearings, we say that the magnetic bearings are "compatible." This definition of compatibility allows us to enumerate a large number of good designs via computer verification of the positive definiteness of the support stiffness matrix.

Using the enumeration methodology outlined above we can derive additional embodiments of the present preferred invention. Alternative embodiments are:

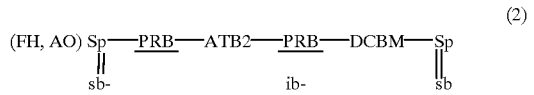

(2)

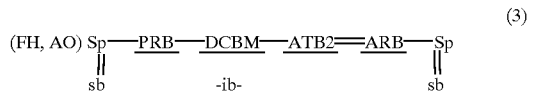

(3)

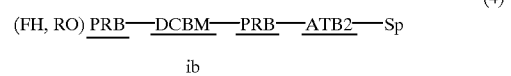

(4)

Additional good embodiments have the following formulas.

Having isolated thrust bearing:

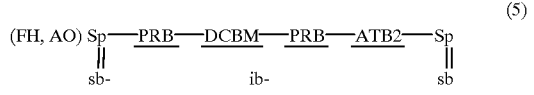

(5)

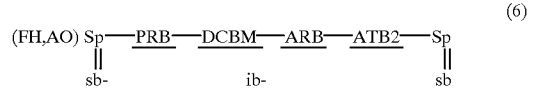

(6)

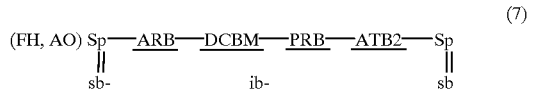

(7)

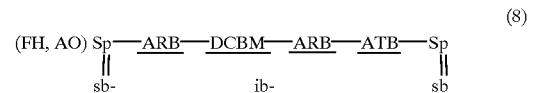

(8)

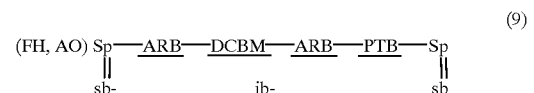

(9)

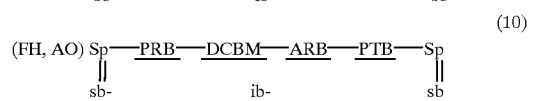

(10)

Having outboard motor:

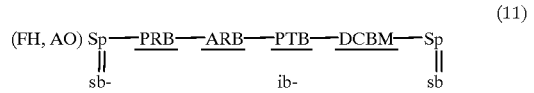

(11)

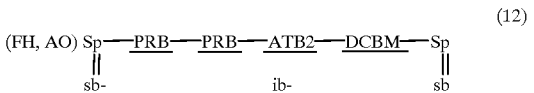

(12)

The geometric configurations of the impeller and stator member are crucial to the hydrodynamic performance and the bio-compatibility of the rotary pump. Specifically, the pump must be designed to avoid regions of high stress which may damage cells or activate the clotting process. Further, regions of blood stagnation that may result in depositions of blood elements on the blood pump structure should also be avoided because they may cause embolism and possibly stroke. A computational fluid dynamics method is employed to design the geometric configurations of the impeller, stator member, and the housing which takes into consideration the specific characteristics of blood flow, such as the tendency of blood to clot when regions of stagnation develop, and the propensity of blood cells to rupture when excessive stress is placed thereon.

Figure 29:
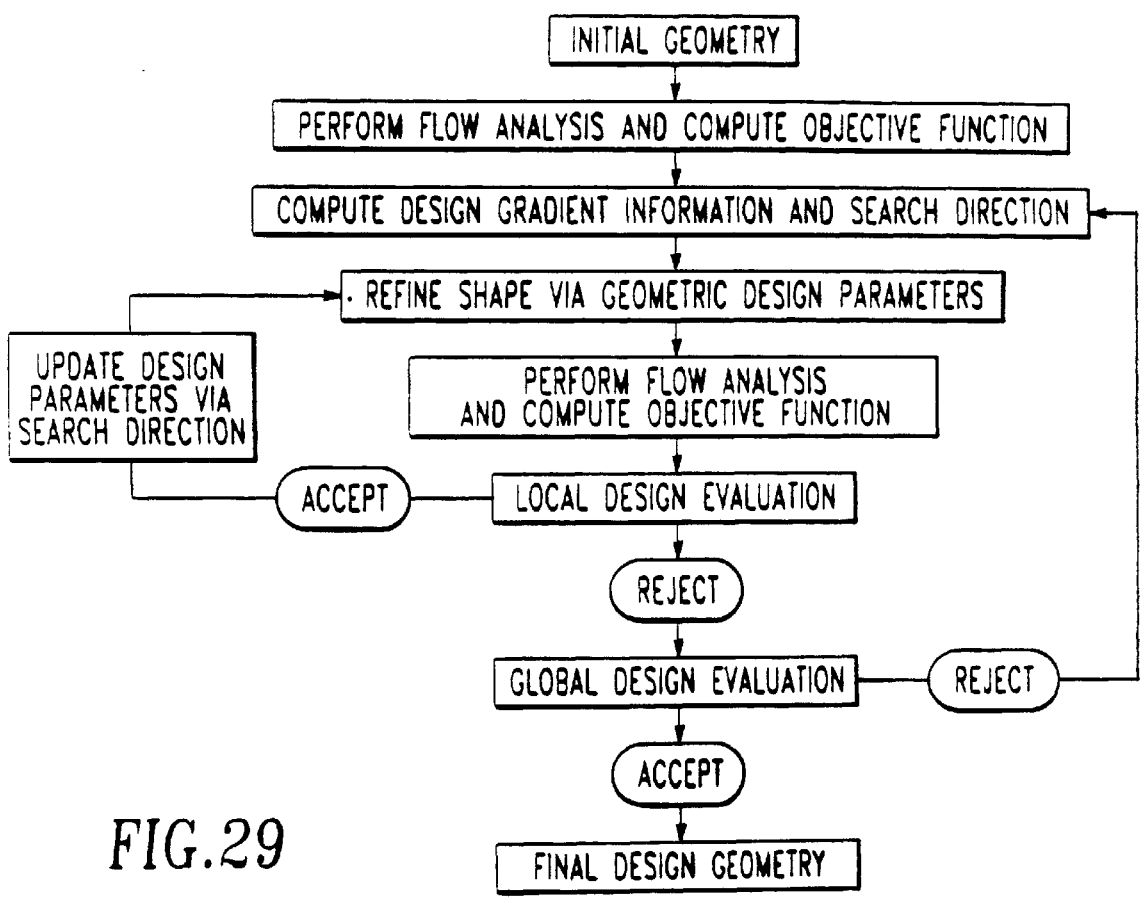
FIG. 29 is a flow chart illustrating a computational fluid dynamics method used to design the geometric configuration of the embodiments of the present preferred invention.

FIG. 29 illustrates a flow chart describing the computational fluid dynamics-based method used to design the geometric configurations of the present preferred invention. This method for designing a rotary fluid pump substantially comprises the steps of: (a) selecting an initial geometric configuration of a part of a rotary fluid pump; (b) converting the geometric configuration into parametric form; (c) selecting a fluid dynamic model for blood flow; (d) choosing an objective functions to be minimized; (e) determining the flow solution and value of the objective function for the initial geometric configuration; (f) determining the sensitivity coefficients and design search direction for the initial geometric configuration both of which are based on gradients of the objective function; (g) selecting a second geometric configuration of the part of the fluid pump being designed by changing the geometric design parameters using the search direction information; (h) determining the flow solution and value of objective function for the second geometric configuration; (i) comparing the objective function for the first geometric configuration with the objective function for the second geometric configuration; (j) if the objective function for the second geometric configuration is less than the objective function for the first geometric configuration, the second geometric configuration becomes the initial geometric configuration and steps (g) through (j) should be performed until the objective function for the second geometric configuration is greater than the objective function for the initial geometric configuration, the global design criteria should then be evaluated; (k) if the global design criteria indicates that further design improvement may be possible, the second geometric configuration becomes the initial geometric configuration and steps (f) through (k) should be performed until no further design improvement is deemed possible; alternatively, the initial design configuration is taken to represent the final design configuration. The final geometric configuration defines the shape of the part of the rotary pump that minimizes stagnant and traumatic flow through the pump. This method can be used to define one or all of the various parts of a rotary pump such as, the impeller blades, the impeller hub, the stator blades, the stator hub and the housing interior surface.

The model for the blood flow is preferably the incompressible Navier-Stokes and conservation of mass equations. Use of the former equations assumes that blood can be treated as a single phase homogeneous linear viscous fluid. In order to solve this equation, a Galerkin finite-element program was written for this purpose. This program uses quadratic velocity-linear pressure elements within a mixed formulation of the steady equations. These element types are known to be stable and produce approximations of optimal order. The resulting, non-linear algebraic system is solved by a Newton continuation method. Analytical gradients of the objective functions are computed using a direct differentiation method.

The objective function used in the above-method represents the desired design criterion to be minimized. For example, the objective functions relating to trauma and platelet activation include, but are not limited to: shear stress with respect to residence time, viscous energy dissipation rates, particle acceleration, negative pressure causing outgassing or cavitation, and turbulence. The objective functions defining stagnation and deposition include but are not limited to: vorticity, reverse flow (i.e., boundary layer shear locally becoming zero), adverse pressure gradient, the standard deviation of consecutive blade-to-blade axial velocity, and boundary layer transport. This list is illustrative but is not exhaustive of the objective functions that can be utilized in the present preferred method of designing geometric configurations for the rotary pump of the present preferred invention.

Figure 30:
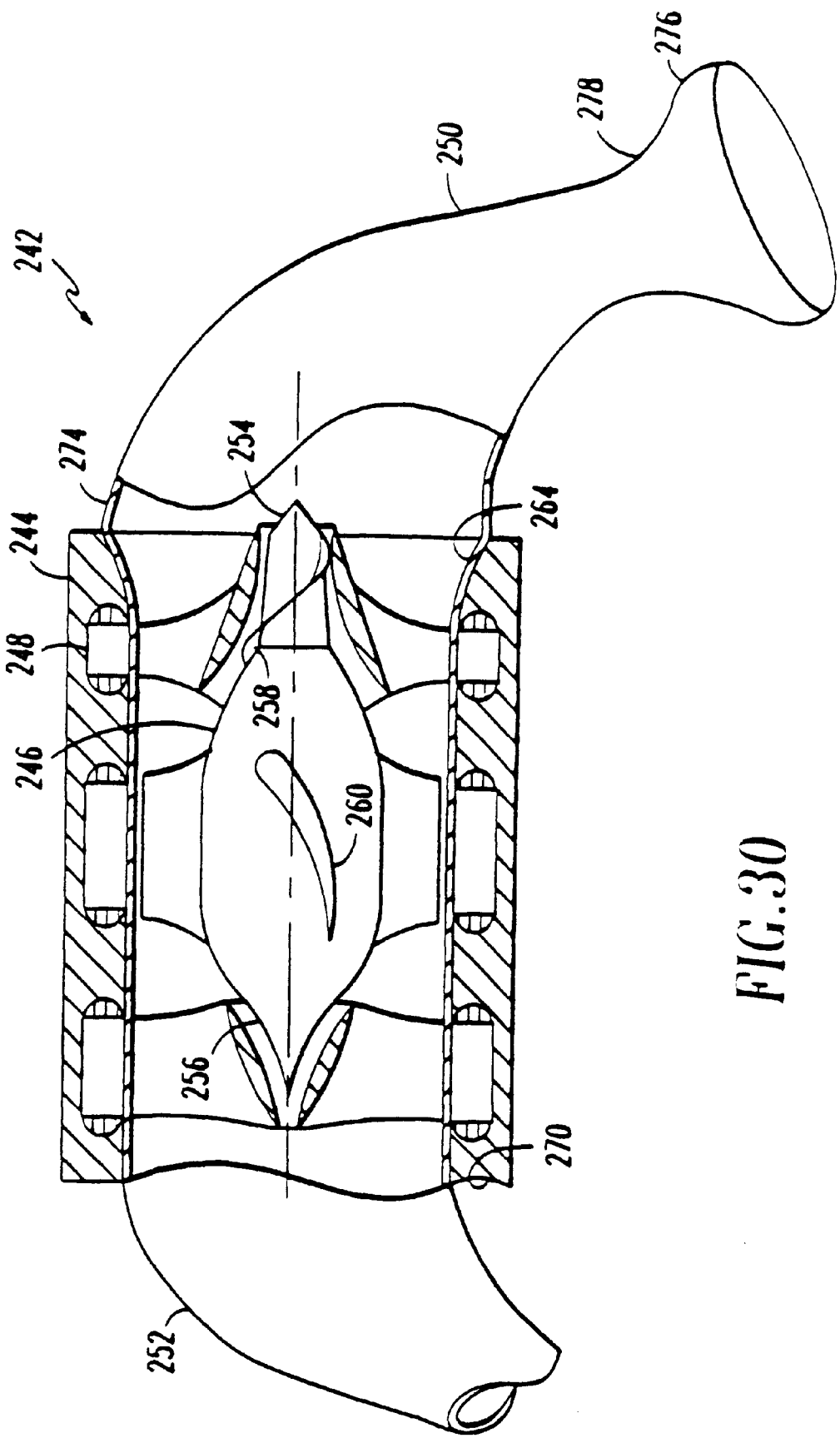
FIG. 30 is a partial cutaway cross-sectional view an alternate embodiment of the rotary fluid pump of the present preferred invention having an inducer blade positioned on the impeller and an inflow cannula and an outflow cannula positioned at the inlet and outlet of the housing, respectively.

FIG. 30 illustrates another embodiment of the present preferred invention which is similar to the rotary pump 10 shown in FIGS. 1 through 5 and can be represented by Formula (1) described above. For purposes of brevity, only the differences between the two rotary pumps will be described. The rotary pump 242 substantially comprises a housing 244, an impeller 246 positioned within the housing 244, a stator member 248, an inflow cannula 250, and an outflow cannula 252, means for levitating the impeller 246 within the housing 244, and means for rotating the impeller 246. The impeller 246 has a nose 254, a tail 256, and an inducer blade 258 positioned on the nose 254 of the impeller 246. The inducer blade 258 extends around the surface of the impeller nose 254. The inducer blade 258, as well as the impeller blades 260 preferably are substantially helical in shape. The inducer blade 258 functions to augment the blood flow through the housing 244 while decreasing cavitation susceptibility. The inflow cannula 250 is attached to the inlet 264 of the housing 244 and the outflow cannula 25:2 is attached to the outlet 270 of the housing 244. The inflow cannula 250 is a conduit with a first end 274 and a second end 276. The first end 274 is attached to the housing inlet 264 and the second end 276 is capable of being attached to the left ventricle of a heart. The second end 276 has a trumpet mouth inlet nozzle 278 with an hourglass exterior configuration. Preferably, the inner diameter of the nozzle 278 tapers from twenty millimeters (20 mm) to a final conduit diameter of twelve millimeters (12 mm). Although both the inflow cannula 250 and the outflow cannula 252 are shown to be integrated into the housing 244 of the rotary pump 242, it is also possible to have cannulae employing quick-connecting mechanisms (not shown) in such that the rotary pump can be quickly detached from the patient.

The stator member 248, the means for rotating the impeller 246 and the means for levitating the impeller function substantially the same as those described in FIGS. 1 through 5. It should also be noted that the rotary pump 242 does not utilize any position sensors as compared to the rotary pump 10, shown in FIGS. 1 through 5, which includes position sensors 65. A sensorless approach, based on back EMF or coil inductance variation is used in this embodiment to measure magnetic bearing gaps and impeller angle. Because there are coils in the motor stator and the magnetic bearing stators, voltages induced by impeller motions and self-induced by coil currents can be used to calculate the impeller angle and the magnetic bearing gaps. Examples of methods of sensorless magnetic bearings and sensorless motor control are described in: "A New Approach To Sensorless and Voltage Controlled AMBs Based on Network Theory Concepts," D. Vischer et al., 2nd International Conference on Magnetic Bearings, Tokyo, pp. 301–309, July, 1990; "Sensorless Magnetic Levitation Control by Measuring the PWM Carrier Frequency Content," Y. Okado, et al., Proceedings of the Third International Symposium on Magnetic Bearings, Alexandria, pp. 176–186, July 1992; "Implementation of Sensorless Control of Radial Magnetic Bearings," R. Gurumoorthy, et al., Proceedings of MAG '95, Alexandria, pp. 239–248, August 1994; and U.S. Pat. No. 5,300,841 issued to M. A. Preston et al., For sensorless DC motor control, see the data sheet from Micro Linear Corporation's ML4425 integrated circuit.

Figure 31:
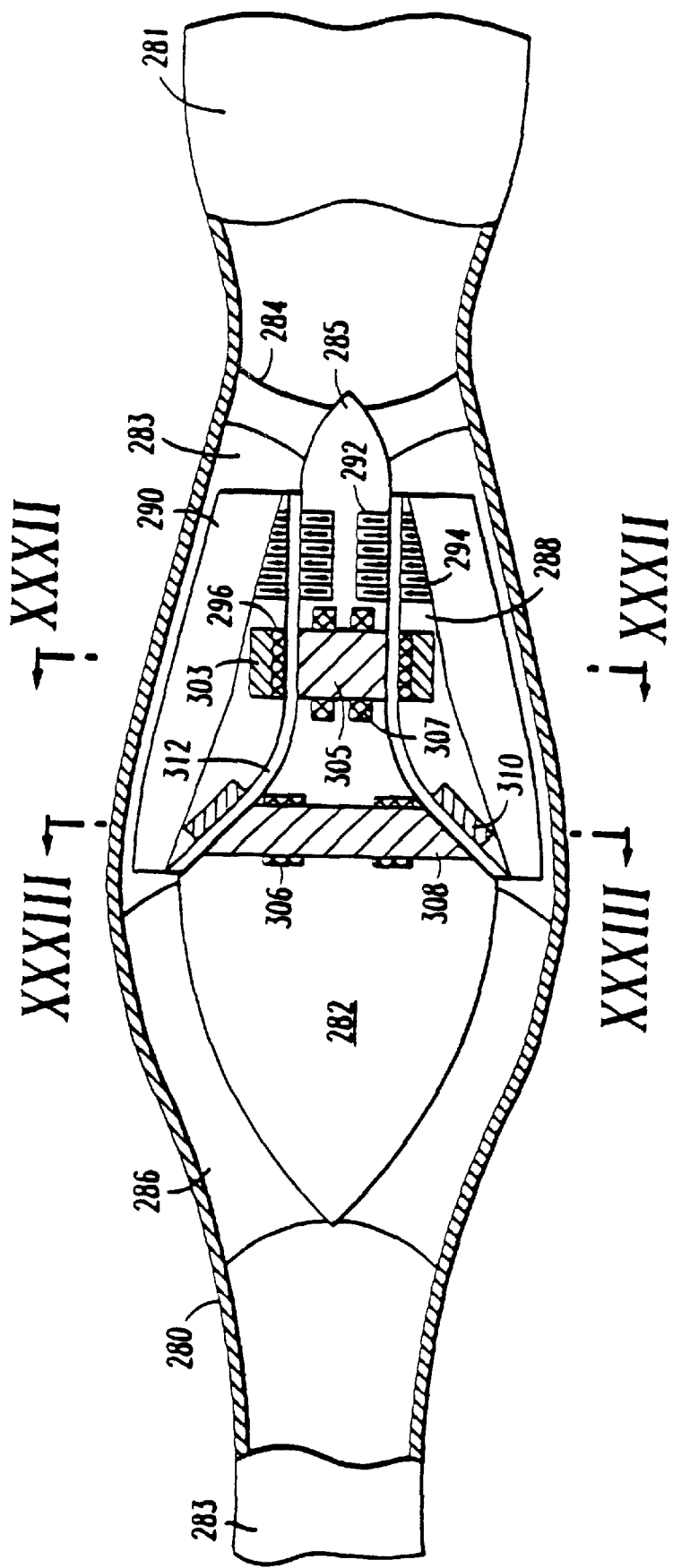
FIG. 31 is a cross-sectional view of an alternate embodiment of the rotary pump of the present preferred invention.
Figure 32:
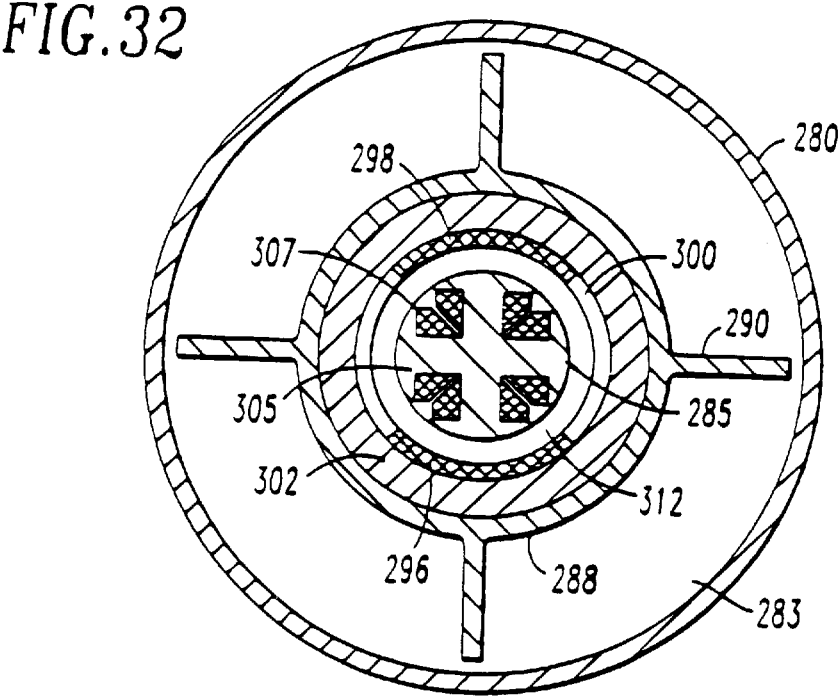
FIG. 32 is a cross-sectional view of the brushless DC motor of the rotary fluid pump shown in FIG. 1 taken along line XXXII—XXXII.
Figure 33:
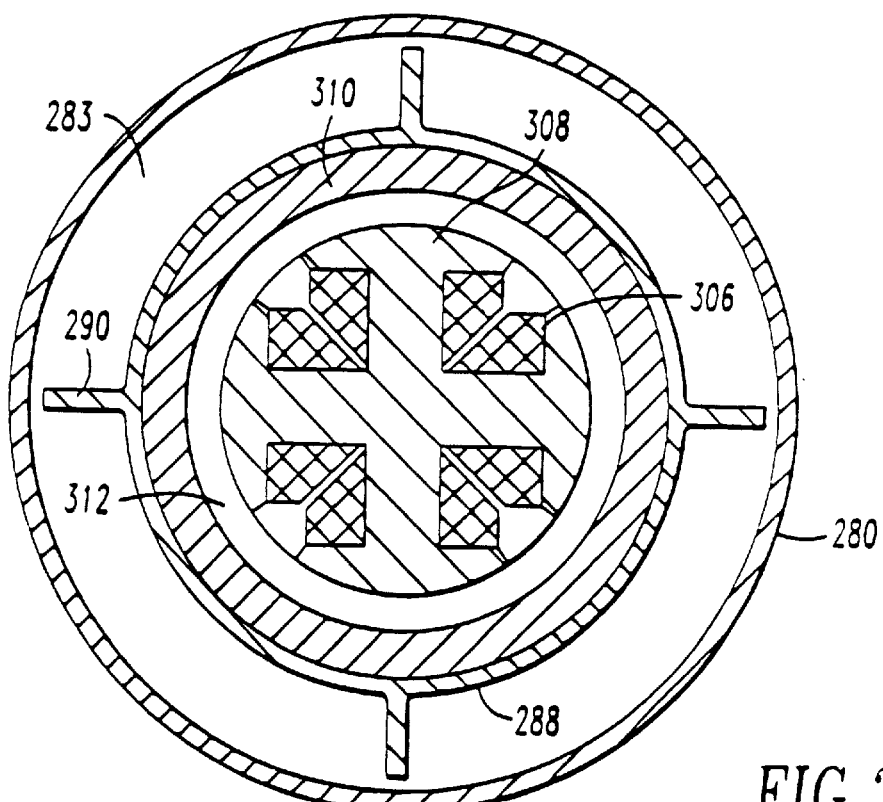
FIG. 33 is a cross-sectional view of the axial conical magnetic bearing of the rotary fluid pump shown in FIG. 31 taken along line XXXIII—XXXIII.

FIGS. 31 through 33 illustrate another embodiment of the present preferred invention which can be described by Formula 3 noted above. The rotary pump of FIGS. 31 through 33 comprises a housing 280 having an inlet 281 and an outlet 283, a stator 282 with an upstream set of stationary blades 284 and a downstream set of stationary blades 286, a substantially cylindrical impeller 288 defining a cavity extending therethrough and having impeller blades 290. The stator 282 is a substantially bell-shaped hub 285. The blood flows primarily through region 283. The conical bearing simultaneously centers the outlet end of the impeller 288 and supplies a thrust force on the impeller 288 in the direction of the outlet. The cylindrical permanent magnet bearing 292 and 294 supplies radial centering forces for the inlet end of the impeller 288. An axial force on the impeller 288 in the direction of the inlet 281 is provided by the same magnetic bearings 292 and 294. This type of bearing is shown in FIG. 7. The axial forces of the permanent magnet bearing and the active conical bearing are balanced via the conical bearing control. The permanent magnet bearing of FIG. 7 is stable in the radial direction, but unstable in the axial. By providing a slight offset as shown in FIG. 7, axial forces can be generated in the direction of the offset.

The means of rotation take the form of a brushless DC motor shown in detail in FIG. 32. The motor has a motor rotor flux return ring 303, stator iron 305 and stator coils 307. Permanent magnets 296 and 298 are magnetized in the radial direction. One inward and one outward creating a two pole motor. Region 300 is non-magnetic material suitable for supporting the permanent magnets. Region 302 is a flux return ring 303 for the motor made from soft magnetic material such as 3% silicon-iron or 50% cobalt-iron. Currents in the stator coils 307 are commuted to affect rotation of the motor. The communication signal is derived from the motor impeller angle through the use of back EMF signals on the coils. This can be accomplished by utilizing an integrated circuit from Micro Linear Corporation.

FIG. 33 is a section through the conical magnetic bearing depicting the coils 306, the stator iron 308 made from soft magnetic material, and the bearing rotor 310 made from soft magnetic material. The surface of the rotor iron interfacing the secondary blood flow region 312 is coated with a biocompatible material. Additionally its surface may be textured with rifling or small impeller blades to enhance blood flow through the region 312.

Figure 34:
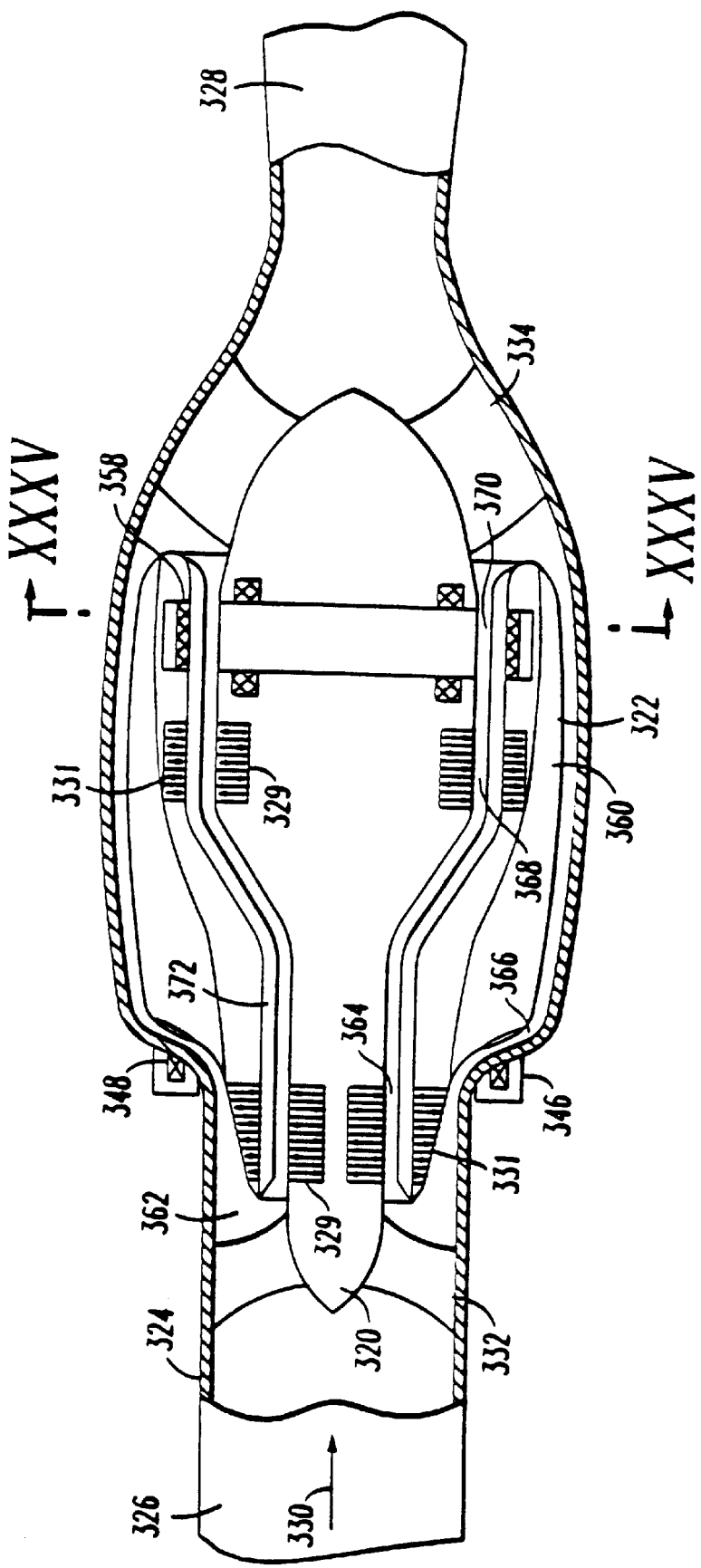
FIG. 34 is another alternate embodiment of the rotary fluid pump of the present preferred invention.
Figure 35:
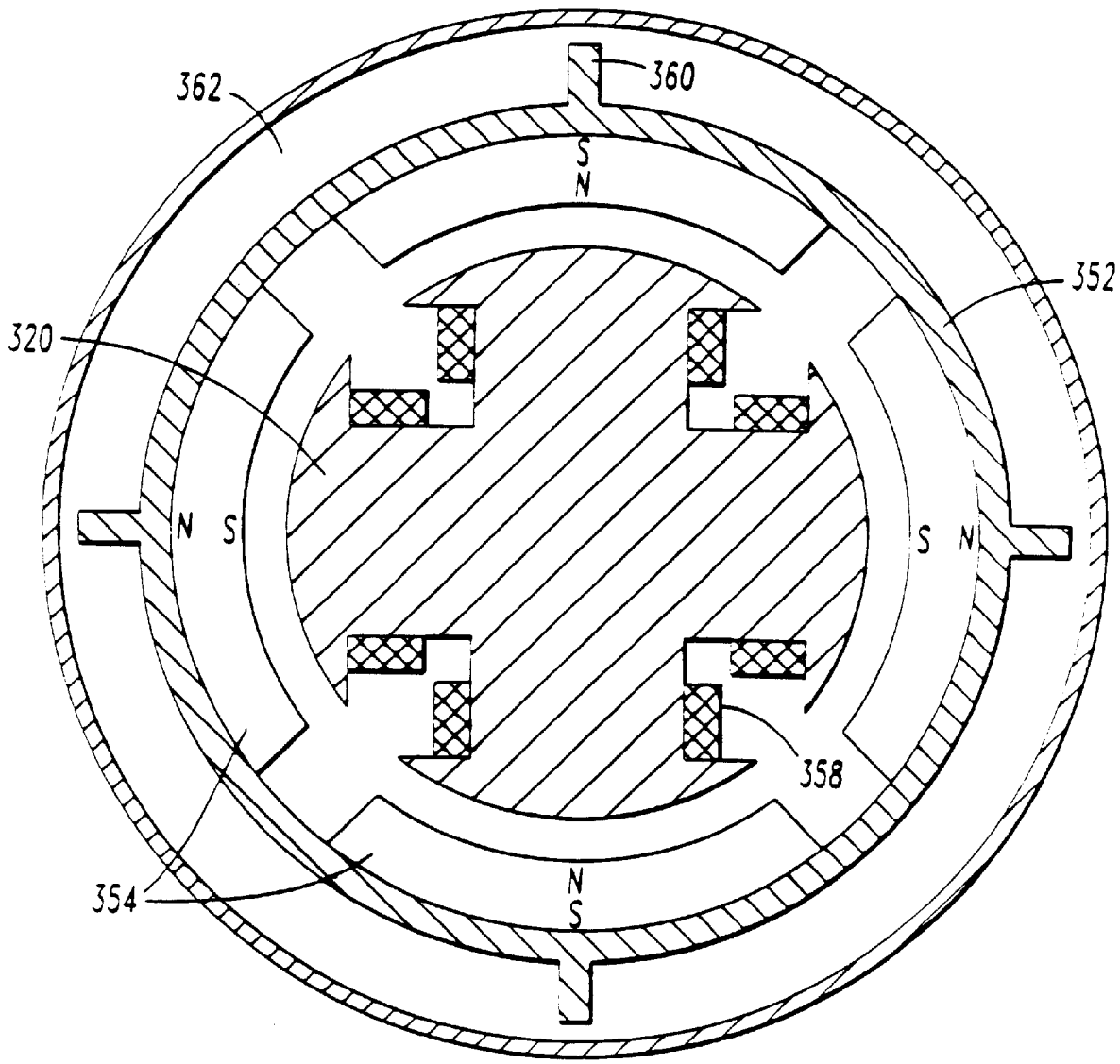
FIG. 35 is the cross-sectional view of the rotary fluid pump of FIG. 34 taken along line XXXV—XXXV.

FIGS. 34 and 35 show another embodiment of the present preferred invention. The advantages of this arrangement is that there is only one active magnetic bearing and a brushless DC motor within an enlarged region of the fixed stator. FIG. 34 illustrates how an ATB2 can be located at the housing. Thus, the motor can use large wire and produce less heat. The rotary comprises a stator 320, an impeller 322 and a housing 324 with an inlet 326 and an outlet 328. The inlet 326 allows blood flow into the pump in the direction 330. The stator 320 is supported by stationary blades 332 at the inlet 326 and stationary blades 334 at the outlet 328. Permanent magnets 329 in the stator 320 and permanent magnets 331 in the impeller 322 support impeller 322 on one end. Permanent magnet 329 in the stator 320 and permanent magnets 331 in the impeller 322 support the impeller 322 at the outlet 328. A thrust bearing stator 346, coil 348 provide support in the axial direction. The rotor forms an annular attachment on the outside of the largely helical impeller blades. Power to rotate the impeller is provided by a DC brushless motor consisting of an iron or other soft magnetic material, rotor ring 352, permanent magnets 354, and a stator coil 358. Blood pumped by the helical impeller blades 360 accelerates the blood through the outlet 328.

Blood flow is partitioned into a primary path 362 and secondary paths through component gaps 364, 366, 368 and 370. The secondary blood flow paths serve the purpose of allowing for non-contact support of the impeller. In order to ensure that blood flows in the proper direction through the magnetic gaps, small blades or rifling may be added as shown at 372.

Figure 36:
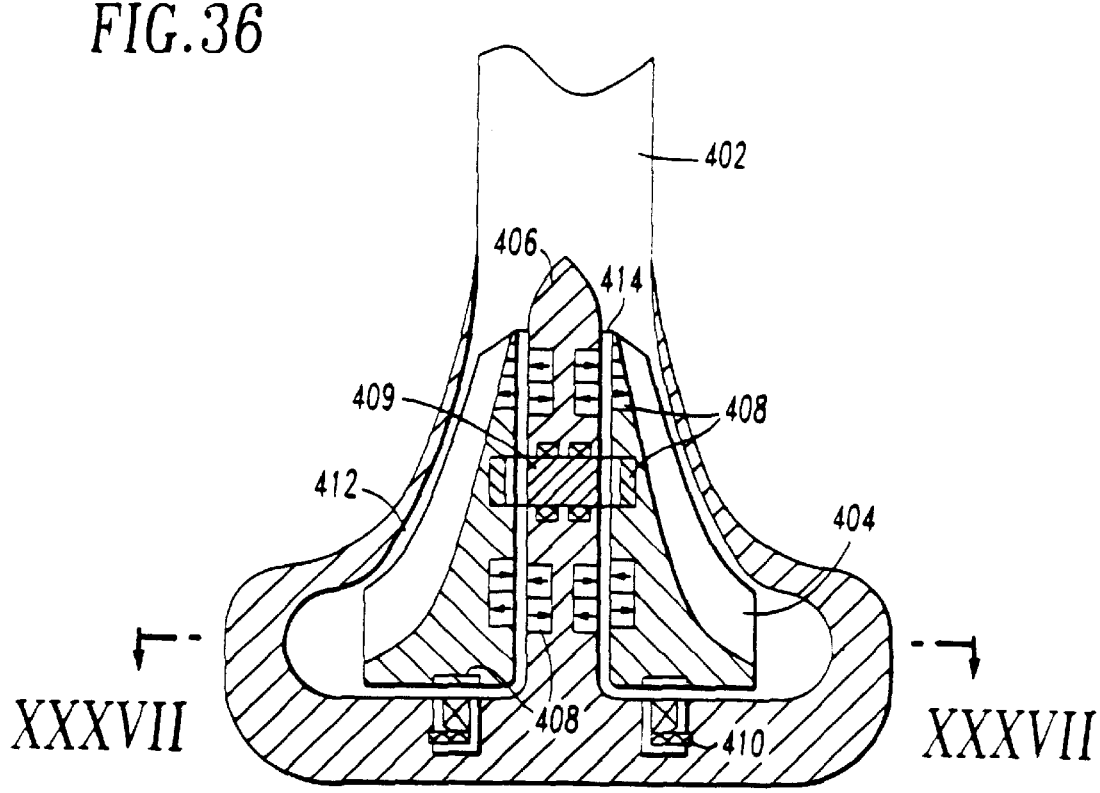
FIG. 36 is a cross-sectional view of another embodiment of the rotary pump of the present invention wherein the rotary pump is takes the form of a centrifugal pump.
Figure 37:
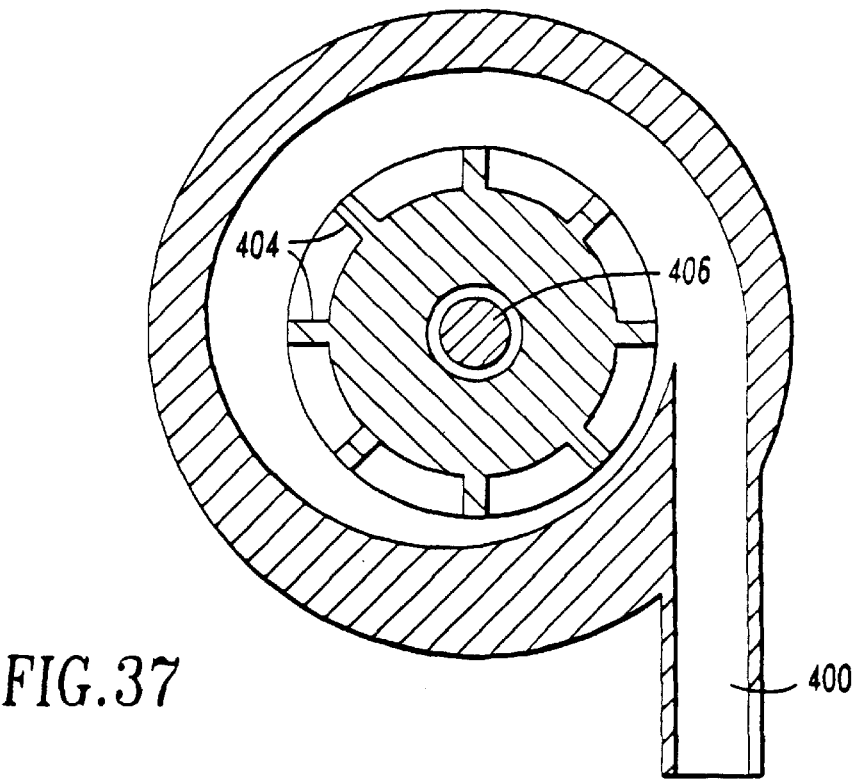
FIG. 37 is a cross-sectional view of the centrifugal pump of FIG. 36 taken along the line XXXVII—XXXVII.

FIGS. 36 and 37 illustrate a centrifugal pump which is a variation of the embodiment shown in FIG. 34 where the outlet 400 is radial instead of axial. The pump comprises a housing 402, an impeller 404, a stator 406 means for levitation 408 and means for rotation 409. Also the thrust bearing is moved to lie downstream from all other magnetic components, and the thrust bearing has a permanent magnet bias magnet 410. Fluid flow gap 412 provides for the primary blood flow through the pump. A secondary fluid flow gap 414 also provides blood flow therethrough; however, gap 414 is small such that efficient levitation is provided.

While the present preferred embodiments and method of making the same have been described herein, it is distinctly understood that the invention is not limited thereto, but may be otherwise variously embodied within the scope of the following claims and any equivalents thereof.

We claim:
1. A device for pumping fluid, comprising:
 (a) a housing having an upstream end a downstream end and an internal region through which said fluid flows when the device is pumping;
 (b) an impeller positioned within said housing and having a substantially conically shaped nose, a substantially conically shaped tail and a mid-section extending between the nose and the tail that has a plurality of substantially helically shaped magnetic impeller blades;
 (c) a stator
  ($c_1$) downstream stator blades extending from the housing such that the impeller tail is axially aligned with the downstream stator, the downstream stator blades being curved to conform to the substantially conically shaped tail, the downstream stator blades being for recovering velocity energy as pressure energy from said fluid exiting said downstream end of said plurality of magnetic impeller blades;
  ($c_2$) upstream stator blades extending from the housing such that the impeller nose is axially aligned within the upstream stator, the upstream stator blades being curved to conform to the substantially conically shaped nose, the upstream stator blades being for directing fluid to the impeller;
 (d) means for levitating said impeller within said housing such that said impeller is substantially centered within said housing and the impeller nose is axially aligned within the upstream stator blades and the impeller tail is axially aligned within the downstream stator blades; and
 (e) means for rotating said impeller which exerts a force on said plurality of magnetic impeller blades.

2. A rotary pump for pumping fluid through a patient comprising:
 (a) a housing having an internal region through which said fluid flows when the rotary pump is pumping;
 (b) an impeller positioned within said housing and having
  ($b_1$) an upstream end and a downstream end;
  ($b_2$) an exterior wall;
  ($b_3$) an interior wall defining a void;
  ($b_4$) a plurality of outboard magnetic impeller blades extending outwardly from the exterior wall which each having an upstream end and a downstream end;

(b₅) a plurality of inboard blades extending inwardly from said interior wall;

(c) a first stator member for recovering velocity energy as pressure energy from said fluid exiting said downstream end of said plurality of impeller blades, said first stator member being attached to said housing;

(d) means for levitating said impeller which substantially centers said impeller within said housing comprising a plurality of electromagnets positioned inside the interior wall of the impeller and outside of the housing and ferromagnetic material disposed within the first stator member; and (e) means for rotating said impeller which exerts a torque on said plurality of outboard magnetic impeller blades causing said impeller to rotate.

3. The rotary pump of claim 2 wherein said first stator member further comprises:

a downstream set of stationary blades which converge around said downstream end of said impeller to define a plurality of fluid flow regions and a downstream passageway and wherein the rotary pump further comprises a second stator member, that is attached to an upstream end of the rotary pump, and comprises an upstream set of stationary blades which converge around said upstream end of said impeller to define a plurality of fluid flow regions and an upstream passageway.

4. The rotary pump of claim 3 wherein said upstream set of stationary blades and said downstream set of stationary blades comprise permanent magnetic material.

5. The rotary pump of claim 3 wherein said impeller is substantially axially symmetric and the impeller upstream end comprises a substantially conical-shaped nose and the impeller downstream end comprises a substantially conical-shaped tail, and wherein the shapes of said upstream passageway and said downstream passageway correspond to the shapes of said conical-shaped nose and said conical-shaped tail, respectively, such that when said impeller nose is positioned within said upstream passageway, a gap is formed between the upstream set of stationary blades and said impeller nose and likewise, when the impeller tail is positioned within said downstream passageway, a gap is formed between said downstream set of stationary blades and said impeller tail.

6. The rotary pump of claim 5 wherein said rotary pump further comprises means for sensing the position of said impeller within said housing and changing the net flux across said gaps in order to move said impeller to the centered position.

7. The rotary pump of claim 3 further comprising an inducer blade which extends around and is attached to said substantially conical-shaped impeller nose.

8. The rotary pump of claim 3, wherein said levitating means comprises a conical electromagnet bearing which includes a plurality of coils, magnetic bearing targets positioned on said impeller, a plurality of backiron segments, and the downstream and upstream sets of stationary blades being magnetic.

9. The rotary pump of claim 8 wherein the levitating means further comprises a plurality of permanent magnets positioned between said plurality of coils and said backiron such that a permanent magnetic bias is provided.

10. The rotary pump of claim 2 wherein said rotating means comprise a brushless DC motor, wherein an electromagnetic field coil extends around the exterior of said housing and adjacent to said plurality of outwardly extending magnetic impeller blades.

11. The rotary pump of claim 2 wherein the rotating means comprises a variable reluctance motor.

12. The rotary pump of claim 2, wherein said outwardly extending plurality of magnetic impeller blades are high-energy-density, rare earth magnet selected from the group consisting of samarium cobalt and neodymium-iron-boron alloy.

13. The rotary pump of claim 2 further comprising an inflow cannula having a first end and a second end, wherein said first end is connected to said housing and said second end substantially has an hourglass configuration and is connectable to a heart.

14. The rotary pump of claim 2, wherein said outwardly extending plurality of magnetic impeller blades are helical in shape.

15. The rotary pump of claim 2, wherein said first stator member has a first portion, a second portion, and a plurality of stationary blades attached to said stator member at said first portion thereof, and wherein said stator member second portion extends axially within said interior wall of said impeller.

16. The rotary pump of claim 15 wherein said first stator member is generally an ellipsoid having a substantially conical-shaped tail and a substantially conical-shaped nose, and said inboard impeller blades are concave such that the curvature thereof corresponds with the curvature of said first stator member.

17. The rotary pump of claim 15 further comprising means for preventing axial movement of said impeller within said housing.

18. The rotary pump of claim 17 wherein the means for preventing axial movement comprises both the impeller and the first stator member having permanent magnets.

19. The rotary pump of claim 18 wherein said outboard impeller blades are helical in shape and the impeller exterior wall generally is tapered in order to pump fluid.

20. The rotary pump of claim 19 wherein the number of said plurality of outboard impeller blades is three.

21. The rotary pump of claim 17 wherein the means for preventing axial movement comprises electromagnets positioned in the first stator member and said impellers, comprising at least a portion which is made from ferromagnetic material.

22. The rotary pump of claim 2, wherein said first stator member has a hub with a first portion and a second portion, a set of upstream stationary blades attached to and extending from said first stator member first portion, and a set of downstream stationary blades attached to and extending from said stator member second portion, wherein said downstream stationary blades and said upstream stationary blades are attached to said housing.

23. The rotary pump of claim 2 further comprising position sensors located on said impeller for detecting axial movement of said impeller.

24. The rotary pump of claim 2 further comprising means for modulating said rotary pump impeller speed in order to create a pulse.

* * * * *